United States Patent [19]

Sivasubramanian et al.

[11] Patent Number: 5,143,905
[45] Date of Patent: Sep. 1, 1992

[54] METHOD AND MEANS FOR EXTENDING THE HOST RANGE OF INSECTICIDAL PROTEINS

[75] Inventors: Natarajan Sivasubramanian; Brian A. Federici, both of Riverside, Calif.

[73] Assignee: The Regents of the University of California, Oakland, Calif.

[21] Appl. No.: 518,575

[22] Filed: May 3, 1990

[51] Int. Cl.$^5$ .................. C07K 3/08; A61K 37/00; A61K 39/07; A61K 39/12
[52] U.S. Cl. .................................... 514/21; 514/8; 514/12; 530/350; 530/409; 424/405; 435/69.7
[58] Field of Search ............... 530/350, 409; 514/21, 514/8, 12; 424/405

[56] References Cited

U.S. PATENT DOCUMENTS 4,870,023  9/1989  Fraser et al. .

OTHER PUBLICATIONS

Schnepf et al., *Journal of Biological Chemistry* 265(34): 20923-20930 (1990).
Oeltmann et al., *Journal of Biological Chemistry* 254(4): 1028-1032 (1979).
Abstract of an oral presentation by Dr. Sivasubramanian at the First Asia-Pacific Conference of Entomology in Thailand (Nov. 8-13 1989).
Hofte et al., *Nucleic Acids Res.* 15, 7183 (1987).
Harrison, B. D. and Murant, A. F., "Involvement of Virus-coded Proteins in Transmission of Plant Viruses by Vectors" in Vectors in Virus Biology, Mayo and Harrap, Eds., Academic Press, 1984, pp. 1-37.
Briddon et al., *Virology* 177, 85-94 (1990).
Wolfsberger et al., *Comp. Biochem. Physiol.* 86A, 301-308 (1987).
Knowles et al., *FEBS Letters* 244, 259-262 (1989).
Honee et al., *Applied and Environm. Microbiol.* 56, 823-825 (1990).
Hofmann et al., *Proc. Natl. Acad. Sci. USA* 85:7844-7848 (1988).
Van Rie et al., *Science* 247:72-74 (1990).
Yamamoto and McLaughlin, *Biochem. Biophys. Res. Commun.* 103:414-421 (1982).
Heierson et al., *J. Bacteriol.* 169:1147-1152 (1987).
Baumann, L. et al., *J. Bacteriol.* 170:2045-2050 (1988).
Bauman, P. et al., *J. Bacteriol.* 169:4061-4067 (1987).
Thomas and Ellar, *FEBS Microbiol. Letters* 154:362-368 (1983).
Thomas and Ellar, *J. Cell Science* 60:181-197 (1983).
Chilcott, C. N. and D. J. Ellar, *Journal of General Microbiology* 134:2551-2558 (1988).
Galjart et al., *Curr. Microbiol.* 16:171-174 (1987).
Waalwijk, C. et al., *Nucleic Acids Res.* 13:8206-8217 (1985).
Goeddel et al., *Nucleic Acids Res.* 8:4057 (1980).
Hitzeman et al., *J. Biol. Chem.* 255:12073 (1980).
Federici et al., The parasporal body of BTI; Structure, Protein Composition, and Toxicity. In "Bacterial Control of Mosquitoes and Blackflies: Biochemistry, Genetics, and Applications of *Bacillus thuringienisis* and *Bacillus sphaericus*" (H. De Barjac and D. Sutherland, editors). Rutgers University Press, New Brunswick, N.J., 1990.
Bitter, G. A., *Methods in Enzymology* 152:673-684 (1987).

(List continued on next page.)

*Primary Examiner*—Howard E. Schain
*Assistant Examiner*—Choon Koh
*Attorney, Agent, or Firm*—Knobbe, Martens, Olson & Bear

[57] ABSTRACT

The invention relates to a method for increasing the host range or toxicity of an insecticidal protein exerting its activity via interaction with the gut epithelium of insects within its host range, by delivering the insecticidal protein to the gut epithelium of a target insect with the aid of an other, targeting protein capable of binding to the gut epithelium of the target insect. The targeting protein may, for example, be of viral origin or, alternatively, may be a bacterial protein or protein domain having high affinity for the lipid components of membranes.

23 Claims, 47 Drawing Sheets

OTHER PUBLICATIONS

Vaeck, M. et al., *Nature* 327:6125, 33-37 (1987).

Fischnoff, D. A. et al., *Biotechnology* 5:807-813 (1987).

Volkman, L. E. and M. D. Summers, *J. Invertebr. Pathol.* 30:102-103 (1977).

Keddie, B. A. and Volkman, L. E., *J. Gen. Virol.* 66:1195-1200 (1985).

Vail, P. V. et al., *J. Invertebr. Pathol.* 21:198-204 (1973); and IVth Int. Colloq. Insect Pathol. (1971).

Ward and Ellar, *J. Mol. Biol.* 191:1-11 (1986).

Davidson and Yamamoto, *Current Microbiol.* 11:171-174 (1984).

Bone et al., *J. Parasitol.* 73:295-299 (1987).

Armstrong et al., *J. Bacteriol.* 161:39-46 (1985).

Ibara and Federici, *J. Bacteriol.* 165:527-533 (1986).

Engvall, E. and Perlman, P., *Immunochem.* 8:871-879 (1971).

Studier, F. W. and B. A. Moffatt, *J. Mol. Biol.* 189:113-130 (1986).

Ward et al., *J. Mol. Biol.* 191:13-22 (1986).

Hofte, Herman and Whitley, H. R., *Microbiological Reviews* 53(2):242-255 (1989).

Ge et al., Proc. Natl. Acad. Sci. USA 86:4037-4041 (1989).

Chow et al., *Applied and Environmental Microbiology*, pp. 2779-2778 (1989).

Adang, Mike et al., *Manipulation of Bacillus thuringiensis Genes for Pest Insect Control* in Proceedings of a Conference held Jul. 18-20, 1988 *Biotech. Biological Pesticides and Novel Plant-Pest Resistance for Insect Pest Management*, Editors: Roberts, D. W. and Granados, R. R., pp. 31-37, Cornell University, New York (1988).

Carlton, Bruce, *Genetic Improvements of Bacillus thuringiensis as a Bioinsecticide* in Proceedings of a Conference held Jul. 18-20, 1988 *Biotech., Biological Pesticides and Novel Plant-Pest Resistance for Insect Pest Management*, Editors: Roberts, D. W. and Granados, R. R., pp. 38-43, Cornell University, New York (1988).

Van Mellaert, Herman et al., *Insecticidal Crystal Proteins from Bacillus thuringiensis: Mode of Action and Expression in Transgenis Plants* in Proceedings of a Conference held Jul. 18-20, 1988 *Biotech., Biological Pesticides and Novel Plant-Pest Resistance for Insect Pest Management*, Editors. Roberts, D. W. and Granados, R. R., pp. 82-87 Cornell University, New York (1988).

```
pT7-7  pfAc13  pfX7  pfAv10  MW
 UI  I   UI  I  UI  I  UI  I  (kD)

FIG. 14a
Nucleotide Sequence of the gp64 gene of AcMNPV

```
                                  -205                             -178
                                       GTCGACTGAGCGTCCGTGTTCATGATCC

-119
CGTTTTTATAACAGCCAGATAAAAATAATCTTATCAATTAAGATAAAAAGATAAGATTA
                              "CAT BOX"
                                                                    -60
TTAATCTAACAACGTGCCTTGTGTCACGTAGGCCAGATAACGGTCGGGTATATAAGATG
                                                       "TATA BOX"
                                                                     -1
CCTCAATGCTACTAGTAAATCAGTCACACCAAGGCTTCAATAAGGAACACACAAGCAAG

+1                                                                15/45
ATG GTA AGC GCT ATT GTT TTA TAT GTG CTT TTG GCG GCG GCG GCG
Met Val Ser Ala Ile Val Leu Tyr Val Leu Leu Ala Ala Ala Ala
================================================================

↓                                        30/90
CAT TCT GCC TTT GCG GCG GAG CAC TGC AAC GCG CAA ATG AAG ACG
His Ser Ala Phe Ala Ala Glu His Cys Asn Ala Gln Met Lys Thr
======================  ****************************************

45/135
GGT CCG TAC AAG ATT AAA AAC TTG GAC ATT ACC CCG CCC AAG GAA
Gly Pro Tyr Lys Ile Lys Asn Leu Asp Ile Thr Pro Pro Lys Glu
****************************************************************

60/180
ACG CTG CAA AAG GAC GTG GAA ATC ACC ATC GTG GAG ACG GAC TAC
Thr Leu Gln Lys Asp Val Glu Ile Thr Ile Val Glu Thr Asp Tyr

75/225
AAC GAA AAC GTG ATT ATC GGC TAC AAG GGG TAC TAC CAG GCG TAT
Asn Glu Asn Val Ile Ile Gly Tyr Lys Gly Tyr Tyr Gln Ala Tyr

90/270
GCG TAC AAC GGC GGC TCG CTG GAT CCC AAC ACA CGC GTC GAA GAA
Ala Tyr Asn Gly Gly Ser Leu Asp Pro Asn Thr Arg Val Glu Glu

105/315
ACC ATG AAA ACG CTG AAT GTG GGC AAA GAG GAT TTG CTC ATG TGG
Thr Met Lys Thr Leu Asn Val Gly Lys Glu Asp Leu Leu Met Trp

120/360
AGC ATC AGG CAG CAG TGC GAG GTG GGC GAA GAG CTG ATC GAC CGT
Ser Ile Arg Gln Gln Cys Glu Val Gly Glu Glu Leu Ile Asp Arg
```

FIG. 14b

```
                                                                135/405
TGG GGC AGT GAC AGC GAC GAC TGT TTT CGC GAC AAC GAG GGC CGC
Trp Gly Ser Asp Ser Asp Asp Cys Phe Arg Asp Asn Glu Gly Arg

150/450
GGC CAG TGG GTC AAA GGC AAA GAG TTG GTG AAG CGG CAG AAT AAC
Gly Gln Trp Val Lys Gly Lys Glu Leu Val Lys Arg Gln Asn Asn

165/495
AAT CAC TTT GCG CAC CAC ACG TGC AAC AAA TCG TGG CGA TGC GGC
Asn His Phe Ala His His Thr Cys Asn Lys Ser Trp Arg Cys Gly
                            ++++++++++++

180/540
ATT TCC ACT TCG AAA ATG TAC AGC AGG CTC GAG TGC CAG GAC GAC
Ile Ser Thr Ser Lys Met Tyr Ser Arg Leu Glu Cys Gln Asp Asp

195/585
ACG GAC GAG TGC CAG GTA TAC ATT TTG GAC GCT GAG GGC AAC CCC
Thr Asp Glu Cys Gln Val Tyr Ile Leu Asp Ala Glu Gly Asn Pro

210/630
ATC AAC GTG ACC GTG GAC ACT GTG CTT CAT CGA GAC GGC GTG AGT
Ile Asn Val Thr Val Asp Thr Val Leu His Arg Asp Gly Val Ser
        ++++++++++++

225/675
ATG ATT CTC AAA CAA AAG TCT ACG TTC ACC ACG CGC CAA ATA AAA
Met Ile Leu Lys Gln Lys Ser Thr Phe Thr Thr Arg Gln Ile Lys

240/720
GCT GCG TGT CTG CTC ATT AAA GAT GAC AAA AAT AAC CCC GAG TCG
Ala Ala Cys Leu Leu Ile Lys Asp Asp Lys Asn Asn Pro Glu Ser

255/765
GTG ACA CGC GAA CAC TGT TTG ATT GAC AAT GAT ATA TAT GAT CTT
Val Thr Arg Glu His Cys Leu Ile Asp Asn Asp Ile Tyr Asp Leu

270/810
TCT AAA AAC ACG TGG AAC TGC AAG TTT AAC AGA TGC ATT AAA CGC
Ser Lys Asn Thr Trp Asn Cys Lys Phe Asn Arg Cys Ile Lys Arg

285/855
AAA GTC GAG CAC CGA GTC AAG AAG CGG CCG CCC ACT TGG CGC CAC
Lys Val Glu His Arg Val Lys Lys Arg Pro Pro Thr Trp Arg His

300/900
AAC GTT AGA GCC AAG TAC ACA GAG GGA GAC ACT GCC ACC AAA GGC
Asn Val Arg Ala Lys Tyr Thr Glu Gly Asp Thr Ala Thr Lys Gly
```

FIG. 14c

```
                                                               315/945
GAC CTG ATG CAT ATT CAA GAG GAG CTG ATG TAC GAA AAC GAT TTG
Asp Leu Met His Ile Gln Glu Glu Leu Met Tyr Glu Asn Asp Leu

330/990
CTG AAA ATG AAC ATT GAG CTG ATG CAT GCG CAC ATC AAC AAG CTA
Leu Lys Met Asn Ile Glu Leu Met His Ala His Ile Asn Lys Leu

345/1035
AAC AAT ATG CTG CAC GAC CTG ATA GTC TCC GTG GCC AAG GTG GAC
Asn Asn Met Leu His Asp Leu Ile Val Ser Val Ala Lys Val Asp

360/1080
GAG CGT TTG ATT GGC AAT CTC ATG AAC AAC TCT GTT TCT TCA ACA
Glu Arg Leu Ile Gly Asn Leu Met Asn Asn Ser Val Ser Ser Thr
                                  ++++++++++++
                                                              375/1125
TTT TTG TCG GAC GAC ACG TTT TTG CTG ATG CCG TGC ACC AAT CCG
Phe Leu Ser Asp Asp Thr Phe Leu Leu Met Pro Cys Thr Asn Pro

390/1170
CCG GCA CAC ACC AGT AAT TGC TAC AAC AAC AGC ATC TAC AAA GAA
Pro Ala His Thr Ser Asn Cys Tyr Asn Asn Ser Ile Tyr Lys Glu
                                  ++++++++++++
                                                              405/1215
GGG CGT TGG GTG GCC AAC ACG GAC TCG TCG CAA TGC ATA GAT TTT
Gly Arg Trp Val Ala Asn Thr Asp Ser Ser Gln Cys Ile Asp Phe

420/1260
AGC AAC TAC AAG GAA CTA GCA ATT GAC GAC GAC GTC GAG TTT TGG
Ser Asn Tyr Lys Glu Leu Ala Ile Asp Asp Asp Val Glu Phe Trp

435/1305
ATC CCG ACC ATC GGC AAC ACG ACC TAT CAC GAC AGT TGG AAA GAT
Ile Pro Thr Ile Gly Asn Thr Thr Tyr His Asp Ser Trp Lys Asp
                              ++++++++++++
                                                              450/1350
GCC AGC GGC TGG TCG TTT ATT GCC CAA CAA AAA AGC AAC CTC ATA
Ala Ser Gly Trp Ser Phe Ile Ala Gln Gln Lys Ser Asn Leu Ile

465/1395
ACC ACC ATG GAG AAC ACC AAG TTT GGC GGC GTC GGC ACC AGT CTG
Thr Thr Met Glu Asn Thr Lys Phe Gly Gly Val Gly Thr Ser Leu

480/1440
AGC GAC ATC ACT TCC ATG GCT GAA GGC GAA TTG GCC GCT AAA TTG
Ser Asp Ile Thr Ser Met Ala Glu Gly Glu Leu Ala Ala Lys Leu
```

FIG. 14d

```
                                                                495/1485
ACT TCG TTC ATG TTT GGT CAT GTA GTT AAC TTT GTA ATT ATA TTA
Thr Ser Phe Met Phe Gly His Val Val Asn Phe Val Ile Ile Leu
~~~~~~~~~~~~~~~~~~~~~~~~~~~~~~~~~~~~~~~~~~~~~~~~~~~~~~~~~~~
                                                                510/1530
ATT GTG ATT TTA TTT TTG TAC TGT ATG ATT AGA AAC CGT AAT AGA
Ile Val Ile Leu Phe Leu Tyr Cys Met Ile Arg Asn Arg Asn Arg
~~~~~~~~~~~~~~~~~~~~~~~~~~~~~~~~~~~~~~~~~~~~~~~
                                                                512/1587
CAA TAT TAAATGTAATAATAAAAATTGTATCATTATTAATGTAATAATAAAAAATTG
Gln Tyr     <polyA>                           <polyA>

1646
TATAGTTTTTAATTGTATATTATAAAATAAAATTTTTAAAATTACAAAGTTTTTTAATA

1705
TCTCAGGCGAGACTTGAACTCACAATTCTAGCAAGATCTATACGATCCAGAGCGCTACG

1764
CTCTACCTTGAGCTACTGAGACGATATGATTATGTTCCAAATAGCGAGTGTGTTGAGAT

1823
TAATAAATGACTGCAGTAGACGCAAGTTCGTTTCTCATACCACAGGCGTTTATGTTTTG

1882
TTGTACCCTGAAAAATCCGTCCTCTCCCCAATCCGTGCCCCAAGTGTTTTTAAAGGTCC

1941
AATATGGAATGTTGTTTTCAACACCATAACCCACTAAAAGAACCGCATGGTTTAGACCG

2000
CTGTTGAAACAATATTTTATAATACCCTGTTTATAGTTAACAATGTCGGCAGCGTCTAT

2059
GGCCATAGGAATAGGGCCGACAAGGCGTAACAAATCTTTAAGTTTTTCCTCGTACACGG

2118
TAATGTATCTATAACAATCTTTTACTTGAACTAGAAACTTATTGGAGTTCATACGGCAA

2177
TTGTTATTGTCTGCTTCGTATGGATAGTCGCTTTCCAGCTGTACGCCGCCCATTTTAAT

2228
GATGGCTTCGAACGCTGTGTGCAACAAGCCGCCGTTACAGCCAGCGTCGAC
```

FIG. 16a pFAv10 = 125 kD fusion protein sequence:

pT7-7/SX12/AvaII(gp64) [2392-5694] ->1-phase Translation

DNA sequence 6071 b.p.AAATCAAATCTAA.. AACATGAGAATT Circular

```
2392/1                                                           2436/15
atg gct aga att cgc gcc cgg gga tcc tct aga gtc gat cga cct
Met Ala Arg Ile Arg Ala Arg Gly Ser Ser Arg Val Asp Arg Pro 2481/30
gCA GAT AAT AAT ACG GAA GCA CTA GAT AGC TCT ACA ACA AAA GAT
Ala Asp Asn Asn Thr Glu Ala Leu Asp Ser Ser Thr Thr Lys Asp 2526/45
GTC ATT CAA AAA GGC ATT TCC GTA GTA GGT GAT CTC CTA GGC GTA
Val Ile Gln Lys Gly Ile Ser Val Val Gly Asp Leu Leu Gly Val 2571/60
GTA GGT TTC CCG TTT GGT GGA GCG CTT GTT TCG TTT TAT ACA AAC
Val Gly Phe Pro Phe Gly Gly Ala Leu Val Ser Phe Tyr Thr Asn 2616/75
TTT TTA AAT ACT ATT TGG CCA AGT GAA GAC CCG TGG AAG GCT TTT
Phe Leu Asn Thr Ile Trp Pro Ser Glu Asp Pro Trp Lys Ala Phe 2661/90
ATG GAA CAA GTA GAA GCA TTG ATG GAT CAG AAA ATA GCT GAT TAT
Met Glu Gln Val Glu Ala Leu Met Asp Gln Lys Ile Ala Asp Tyr 2706/105
GCA AAA AAT AAA GCT CTT GCA GAG TTA CAG GGC CTT CAA AAT AAT
Ala Lys Asn Lys Ala Leu Ala Glu Leu Gln Gly Leu Gln Asn Asn 2751/120
GTC GAA GAT TAT GTG AGT GCA TTG AGT TCA TGG CAA AAA AAT CCT
Val Glu Asp Tyr Val Ser Ala Leu Ser Ser Trp Gln Lys Asn Pro 2796/135
GTG AGT TCA CGA AAT CCA CAT AGC CAG GGG CGG ATA AGA GAG CTG
Val Ser Ser Arg Asn Pro His Ser Gln Gly Arg Ile Arg Glu Leu 2841/150
TTT TCT CAA GCA GAA AGT CAT TTT CGT AAT TCA ATG CCT TCG TTT
Phe Ser Gln Ala Glu Ser His Phe Arg Asn Ser Met Pro Ser Phe
```

FIG. 16b

```
                                                              2886/165
GCA ATT TCT GGA TAC GAG GTT CTA TTT CTA ACA ACA TAT GCA CAA
Ala Ile Ser Gly Tyr Glu Val Leu Phe Leu Thr Thr Tyr Ala Gln

2931/180
GCT GCC AAC ACA CAT TTA TTT TTA CTA AAA GAC GCT CAA ATT TAT
Ala Ala Asn Thr His Leu Phe Leu Leu Lys Asp Ala Gln Ile Tyr

2976/195
GGA GAA GAA TGG GGA TAC GAA AAA GAA GAT ATT GCT GAA TTT TAT
Gly Glu Glu Trp Gly Tyr Glu Lys Glu Asp Ile Ala Glu Phe Tyr

3021/210
AAA AGA CAA CTA AAA CTT ACG CAA GAA TAT ACT GAC CAT TGT GTC
Lys Arg Gln Leu Lys Leu Thr Gln Glu Tyr Thr Asp His Cys Val

3066/225
AAA TGG TAT AAT GTT GGA TTA GAT AAA TTA AGA GGT TCA TCT TAT
Lys Trp Tyr Asn Val Gly Leu Asp Lys Leu Arg Gly Ser Ser Tyr

3111/240
GAA TCT TGG GTA AAC TTT AAC CGT TAT CGC AGA GAG ATG ACA TTA
Glu Ser Trp Val Asn Phe Asn Arg Tyr Arg Arg Glu Met Thr Leu

3156/255
ACA GTA TTA GAT TTA ATT GCA CTA TTT CCA TTG TAT GAT GTT CGG
Thr Val Leu Asp Leu Ile Ala Leu Phe Pro Leu Tyr Asp Val Arg

3201/270
CTA TAC CCA AAA GAA GTT AAA ACC GAA TTA ACA AGA GAC GTT TTA
Leu Tyr Pro Lys Glu Val Lys Thr Glu Leu Thr Arg Asp Val Leu

3246/285
ACA GAT CCA ATT GTC GGA GTC AAC AAC CTT AGG GGC TAT GGA ACA
Thr Asp Pro Ile Val Gly Val Asn Asn Leu Arg Gly Tyr Gly Thr

3291/300
ACC TTC TCT AAT ATA GAA AAT TAT ATT CGA AAA CCA CAT CTA TTT
Thr Phe Ser Asn Ile Glu Asn Tyr Ile Arg Lys Pro His Leu Phe

3336/315
GAC TAT CTG CAT AGA ATT CAA TTT CAC ACG CGG TTC CAA CCA GGA
Asp Tyr Leu His Arg Ile Gln Phe His Thr Arg Phe Gln Pro Gly

3381/330
TAT TAT GGA AAT GAC TCT TTC AAT TAT TGG TCC GGT AAT TAT GTT
Tyr Tyr Gly Asn Asp Ser Phe Asn Tyr Trp Ser Gly Asn Tyr Val
```

FIG. 16c

```
                                                                3426/345
TCA ACT AGA CCA AGC ATA GGA TCA AAT GAT ATA ATC ACA TCT CCA
Ser Thr Arg Pro Ser Ile Gly Ser Asn Asp Ile Ile Thr Ser Pro

3471/360
TTC TAT GGA AAT AAA TCC AGT GAA CCT GTA CAA AAT TTA GAA TTT
Phe Tyr Gly Asn Lys Ser Ser Glu Pro Val Gln Asn Leu Glu Phe

3516/375
AAT GGA GAA AAA GTC TAT AGA GCC GTA GCA AAT ACA AAT CTT GCG
Asn Gly Glu Lys Val Tyr Arg Ala Val Ala Asn Thr Asn Leu Ala

3561/390
GTC TGG CCG TCC GCT GTA TAT TCA GGT GTT ACA AAA GTG GAA TTT
Val Trp Pro Ser Ala Val Tyr Ser Gly Val Thr Lys Val Glu Phe

3606/405
AGC CAA TAT AAT GAT CAA ACA GAT GAA GCA AGT ACA CAA ACG TAC
Ser Gln Tyr Asn Asp Gln Thr Asp Glu Ala Ser Thr Gln Thr Tyr

3651/420
GAC TCA AAA AGA AAT GTT GGC GCG GTC AGC TGG GAT TCT ATC GAT
Asp Ser Lys Arg Asn Val Gly Ala Val Ser Trp Asp Ser Ile Asp

3696/435
CAA TTG CCT CCA GAA ACA ACA GAT GAA CCT CTA GAA AAG GGA TAT
Gln Leu Pro Pro Glu Thr Thr Asp Glu Pro Leu Glu Lys Gly Tyr

3741/450
AGC CAT CAA CTC AAT TAT GTA ATG TGC TTT TTA ATG CAG GGT AGT
Ser His Gln Leu Asn Tyr Val Met Cys Phe Leu Met Gln Gly Ser

3786/465
AGA GGA ACA ATC CCA GTG TTA ACT TGG ACA CAT AAA AGT GTA GAC
Arg Gly Thr Ile Pro Val Leu Thr Trp Thr His Lys Ser Val Asp

3831/480
TTT TTT AAC ATG ATT GAT TCG AAA AAA ATT ACA CAA CTT CCG TTA
Phe Phe Asn Met Ile Asp Ser Lys Lys Ile Thr Gln Leu Pro Leu

3876/495
GTA AAG GCA TAT AAG TTA CAA TCT GGT GCT TCC GTT GTC GCA GGT
Val Lys Ala Tyr Lys Leu Gln Ser Gly Ala Ser Val Val Ala Gly

3921/510
CCT AGG TTT ACA GGA GGA GAT ATC ATT CAA TGC ACA GAA AAT GGA
Pro Arg Phe Thr Gly Gly Asp Ile Ile Gln Cys Thr Glu Asn Gly
```

FIG. 16d

```
                                                      3966/525
AGT GCG GCA ACT ATT TAC GTT ACA CCG GAT GTG TCG TAC TCT CAA
Ser Ala Ala Thr Ile Tyr Val Thr Pro Asp Val Ser Tyr Ser Gln

4011/540
AAA TAT CGA GCT AGA ATT CAT TAT GCT TCT ACA TCT CAG ATA ACA
Lys Tyr Arg Ala Arg Ile His Tyr Ala Ser Thr Ser Gln Ile Thr

4056/555
TTT ACA CTC AGT TTA GAC GGG GCA CCA TTT AAT CAA TAC TAT TTC
Phe Thr Leu Ser Leu Asp Gly Ala Pro Phe Asn Gln Tyr Tyr Phe

4101/570
GAT AAA ACG ATA AAT AAA GGA GAC ACA TTA ACG TAT AAT TCA TTT
Asp Lys Thr Ile Asn Lys Gly Asp Thr Leu Thr Tyr Asn Ser Phe

4146/585
AAT TTA GCA AGT TTC AGC ACA CCA TTC GAA TTA TCA GGG AAT AAC
Asn Leu Ala Ser Phe Ser Thr Pro Phe Glu Leu Ser Gly Asn Asn

4191/600
TTA CAA ATA GGC GTC ACA GGA TTA AGT GCT GGA GAT AAA GTT TAT
Leu Gln Ile Gly Val Thr Gly Leu Ser Ala Gly Asp Lys Val Tyr

4236/615
ATA GAC AAA ATT GAA TTg ggg atc gat cct cta gag tcg acc tgc
Ile Asp Lys Ile Glu Leu Gly Ile Asp Pro Leu Glu Ser Thr Cys 4281/630
agc cca agc tGT CCG TAC AAG ATT AAA AAC TTG GAC ATT ACC CCG
Ser Pro Ser Cys Pro Tyr Lys Ile Lys Asn Leu Asp Ile Thr Pro 4326/645
CCC AAG GAA ACG CTG CAA AAG GAC GTG GAA ATC ACC ATC GTG GAG
Pro Lys Glu Thr Leu Gln Lys Asp Val Glu Ile Thr Ile Val Glu 4371/660
ACG GAC TAC AAC GAA AAC GTG ATT ATC GGC TAC AAG GGG TAC TAC
Thr Asp Tyr Asn Glu Asn Val Ile Ile Gly Tyr Lys Gly Tyr Tyr 4416/675
CAG GCG TAT GCG TAC AAC GGC GGC TCG CTG GAT CCC AAC ACA CGC
Gln Ala Tyr Ala Tyr Asn Gly Gly Ser Leu Asp Pro Asn Thr Arg 4461/690
GTC GAA GAA ACC ATG AAA ACG CTG AAT GTG GGC AAA GAG GAT TTG
Val Glu Glu Thr Met Lys Thr Leu Asn Val Gly Lys Glu Asp Leu
```

FIG. 16e

```
                                                                  4506/705
CTC ATG TGG AGC ATC AGG CAG CAG TGC GAG GTG GGC GAA GAG CTG
Leu Met Trp Ser Ile Arg Gln Gln Cys Glu Val Gly Glu Glu Leu

4551/720
ATC GAC CGT TGG GGC AGT GAC AGC GAC GAC TGT TTT CGC GAC AAC
Ile Asp Arg Trp Gly Ser Asp Ser Asp Asp Cys Phe Arg Asp Asn

4596/735
GAG GGC CGC GGC CAG TGG GTC AAA GGC AAA GAG TTG GTG AAG CGG
Glu Gly Arg Gly Gln Trp Val Lys Gly Lys Glu Leu Val Lys Arg

4641/750
CAG AAT AAC AAT CAC TTT GCG CAC CAC ACG TGC AAC AAA TCG TGG
Gln Asn Asn Asn His Phe Ala His His Thr Cys Asn Lys Ser Trp

4686/765
CGA TGC GGC ATT TCC ACT TCG AAA ATG TAC AGC AGG CTC GAG TGC
Arg Cys Gly Ile Ser Thr Ser Lys Met Tyr Ser Arg Leu Glu Cys

4731/780
CAG GAC GAC ACG GAC GAG TGC CAG GTA TAC ATT TTG GAC GCT GAG
Gln Asp Asp Thr Asp Glu Cys Gln Val Tyr Ile Leu Asp Ala Glu

4776/795
GGC AAC CCC ATC AAC GTG ACC GTG GAC ACT GTG CTT CAT CGA GAC
Gly Asn Pro Ile Asn Val Thr Val Asp Thr Val Leu His Arg Asp

4821/810
GGC GTG AGT ATG ATT CTC AAA CAA AAG TCT ACG TTC ACC ACG CGC
Gly Val Ser Met Ile Leu Lys Gln Lys Ser Thr Phe Thr Thr Arg

4866/825
CAA ATA AAA GCT GCG TGT CTG CTC ATT AAA GAT GAC AAA AAT AAC
Gln Ile Lys Ala Ala Cys Leu Leu Ile Lys Asp Asp Lys Asn Asn

4911/840
CCC GAG TCG GTG ACA CGC GAA CAC TGT TTG ATT GAC AAT GAT ATA
Pro Glu Ser Val Thr Arg Glu His Cys Leu Ile Asp Asn Asp Ile

4956/855
TAT GAT CTT TCT AAA AAC ACG TGG AAC TGC AAG TTT AAC AGA TGC
Tyr Asp Leu Ser Lys Asn Thr Trp Asn Cys Lys Phe Asn Arg Cys

5001/870
ATT AAA CGC AAA GTC GAG CAC CGA GTC AAG AAG CGG CCG CCC ACT
Ile Lys Arg Lys Val Glu His Arg Val Lys Lys Arg Pro Pro Thr
```

FIG. 16f

```
                                                                  5046/885
TGG CGC CAC AAC GTT AGA GCC AAG TAC ACA GAG GGA GAC ACT GCC
Trp Arg His Asn Val Arg Ala Lys Tyr Thr Glu Gly Asp Thr Ala

5091/900
ACC AAA GGC GAC CTG ATG CAT ATT CAA GAG GAG CTG ATG TAC GAA
Thr Lys Gly Asp Leu Met His Ile Gln Glu Glu Leu Met Tyr Glu

5136/915
AAC GAT TTG CTG AAA ATG AAC ATT GAG CTG ATG CAT GCG CAC ATC
Asn Asp Leu Leu Lys Met Asn Ile Glu Leu Met His Ala His Ile

5181/930
AAC AAG CTA AAC AAT ATG CTG CAC GAC CTG ATA GTC TCC GTG GCC
Asn Lys Leu Asn Asn Met Leu His Asp Leu Ile Val Ser Val Ala

5226/945
AAG GTG GAC GAG CGT TTG ATT GGC AAT CTC ATG AAC AAC TCT GTT
Lys Val Asp Glu Arg Leu Ile Gly Asn Leu Met Asn Asn Ser Val

5271/960
TCT TCA ACA TTT TTG TCG GAC GAC ACG TTT TTG CTG ATG CCG TGC
Ser Ser Thr Phe Leu Ser Asp Asp Thr Phe Leu Leu Met Pro Cys

5316/975
ACC AAT CCG CCG GCA CAC ACC AGT AAT TGC TAC AAC AAC AGC ATC
Thr Asn Pro Pro Ala His Thr Ser Asn Cys Tyr Asn Asn Ser Ile

5361/990
TAC AAA GAA GGG CGT TGG GTG GCC AAC ACG GAC TCG TCG CAA TGC
Tyr Lys Glu Gly Arg Trp Val Ala Asn Thr Asp Ser Ser Gln Cys

5406/1005
ATA GAT TTT AGC AAC TAC AAG GAA CTA GCA ATT GAC GAC GAC GTC
Ile Asp Phe Ser Asn Tyr Lys Glu Leu Ala Ile Asp Asp Asp Val

5451/1020
GAG TTT TGG ATC CCG ACC ATC GGC AAC ACG ACC TAT CAC GAC AGT
Glu Phe Trp Ile Pro Thr Ile Gly Asn Thr Thr Tyr His Asp Ser

5496/1035
TGG AAA GAT GCC AGC GGC TGG TCG TTT ATT GCC CAA CAA AAA AGC
Trp Lys Asp Ala Ser Gly Trp Ser Phe Ile Ala Gln Gln Lys Ser

5541/1050
AAC CTC ATA ACC ACC ATG GAG AAC ACC AAG TTT GGC GGC GTC GGC
Asn Leu Ile Thr Thr Met Glu Asn Thr Lys Phe Gly Gly Val Gly
```

FIG. 16g

```
                                                                5586/1065
ACC AGT CTG AGC GAC ATC ACT TCC ATG GCT GAA GGC GAA TTG GCC
Thr Ser Leu Ser Asp Ile Thr Ser Met Ala Glu Gly Glu Leu Ala

5631/1080
GCT AAA TTG ACT TCG TTC ATG TTT GGT CAT GTA GTT AAC TTT GTA
Ala Lys Leu Thr Ser Phe Met Phe Gly His Val Val Asn Phe Val

5676/1095
ATT ATA TTA ATT GTG ATT TTA TTT TTG TAC TGT ATG ATT AGA AAC
Ile Ile Leu Ile Val Ile Leu Phe Leu Tyr Cys Met Ile Arg Asn

5694/1101
CGT AAT AGA CAA TAT TAA
Arg Asn Arg Gln Tyr OCH
```

FIG. 17a pFX7 = 108 kD fusion protein sequence pT7-7/SX12/Xho1(gp64) [2392 to 5262] -> 1-Phase Translation

DNA sequence 5442 b. p. AAATCAATCTAA... AACATGAGAATT Circular

```
2392/1                                                          2436/15
atg gct aga att cgc gcc cgg gga tcc tct aga gtc gat cga cct
Met Ala Arg Ile Arg Ala Arg Gly Ser Ser Arg Val Asp Arg Pro 2481/30
gCA GAT AAT AAT ACG GAA GCA CTA GAT AGC TCT ACA ACA AAA GAT
Ala Asp Asn Asn Thr Glu Ala Leu Asp Ser Ser Thr Thr Lys Asp 2526/45
GTC ATT CAA AAA GGC ATT TCC GTA GTA GGT GAT CTC CTA GGC GTA
Val Ile Gln Lys Gly Ile Ser Val Val Gly Asp Leu Leu Gly Val 2571/60
GTA GGT TTC CCG TTT GGT GGA GCG CTT GTT TCG TTT TAT ACA AAC
Val Gly Phe Pro Phe Gly Gly Ala Leu Val Ser Phe Tyr Thr Asn 2616/75
TTT TTA AAT ACT ATT TGG CCA AGT GAA GAC CCG TGG AAG GCT TTT
Phe Leu Asn Thr Ile Trp Pro Ser Glu Asp Pro Trp Lys Ala Phe 2661/90
ATG GAA CAA GTA GAA GCA TTG ATG GAT CAG AAA ATA GCT GAT TAT
Met Glu Gln Val Glu Ala Leu Met Asp Gln Lys Ile Ala Asp Tyr 2706/105
GCA AAA AAT AAA GCT CTT GCA GAG TTA CAG GGC CTT CAA AAT AAT
Ala Lys Asn Lys Ala Leu Ala Glu Leu Gln Gly Leu Gln Asn Asn 2751/120
GTC GAA GAT TAT GTG AGT GCA TTG AGT TCA TGG CAA AAA AAT CCT
Val Glu Asp Tyr Val Ser Ala Leu Ser Ser Trp Gln Lys Asn Pro 2796/135
GTG AGT TCA CGA AAT CCA CAT AGC CAG GGG CGG ATA AGA GAG CTG
Val Ser Ser Arg Asn Pro His Ser Gln Gly Arg Ile Arg Glu Leu 2841/150
TTT TCT CAA GCA GAA AGT CAT TTT CGT AAT TCA ATG CCT TCG TTT
Phe Ser Gln Ala Glu Ser His Phe Arg Asn Ser Met Pro Ser Phe
```

FIG. 17b

```
                                                              2886/165
GCA ATT TCT GGA TAC GAG GTT CTA TTT CTA ACA ACA TAT GCA CAA
Ala Ile Ser Gly Tyr Glu Val Leu Phe Leu Thr Thr Tyr Ala Gln

2931/180
GCT GCC AAC ACA CAT TTA TTT TTA CTA AAA GAC GCT CAA ATT TAT
Ala Ala Asn Thr His Leu Phe Leu Leu Lys Asp Ala Gln Ile Tyr

2976/195
GGA GAA GAA TGG GGA TAC GAA AAA GAA GAT ATT GCT GAA TTT TAT
Gly Glu Glu Trp Gly Tyr Glu Lys Glu Asp Ile Ala Glu Phe Tyr

3021/210
AAA AGA CAA CTA AAA CTT ACG CAA GAA TAT ACT GAC CAT TGT GTC
Lys Arg Gln Leu Lys Leu Thr Gln Glu Tyr Thr Asp His Cys Val

3066/225
AAA TGG TAT AAT GTT GGA TTA GAT AAA TTA AGA GGT TCA TCT TAT
Lys Trp Tyr Asn Val Gly Leu Asp Lys Leu Arg Gly Ser Ser Tyr

3111/240
GAA TCT TGG GTA AAC TTT AAC CGT TAT CGC AGA GAG ATG ACA TTA
Glu Ser Trp Val Asn Phe Asn Arg Tyr Arg Arg Glu Met Thr Leu

3156/255
ACA GTA TTA GAT TTA ATT GCA CTA TTT CCA TTG TAT GAT GTT CGG
Thr Val Leu Asp Leu Ile Ala Leu Phe Pro Leu Tyr Asp Val Arg

3201/270
CTA TAC CCA AAA GAA GTT AAA ACC GAA TTA ACA AGA GAC GTT TTA
Leu Tyr Pro Lys Glu Val Lys Thr Glu Leu Thr Arg Asp Val Leu

3246/285
ACA GAT CCA ATT GTC GGA GTC AAC AAC CTT AGG GGC TAT GGA ACA
Thr Asp Pro Ile Val Gly Val Asn Asn Leu Arg Gly Tyr Gly Thr

3291/300
ACC TTC TCT AAT ATA GAA AAT TAT ATT CGA AAA CCA CAT CTA TTT
Thr Phe Ser Asn Ile Glu Asn Tyr Ile Arg Lys Pro His Leu Phe

3336/315
GAC TAT CTG CAT AGA ATT CAA TTT CAC ACG CGG TTC CAA CCA GGA
Asp Tyr Leu His Arg Ile Gln Phe His Thr Arg Phe Gln Pro Gly
```

FIG. 17c

```
                                                           3381/330
TAT TAT GGA AAT GAC TCT TTC AAT TAT TGG TCC GGT AAT TAT GTT
Tyr Tyr Gly Asn Asp Ser Phe Asn Tyr Trp Ser Gly Asn Tyr Val

3426/345
TCA ACT AGA CCA AGC ATA GGA TCA AAT GAT ATA ATC ACA TCT CCA
Ser Thr Arg Pro Ser Ile Gly Ser Asn Asp Ile Ile Thr Ser Pro

3471/360
TTC TAT GGA AAT AAA TCC AGT GAA CCT GTA CAA AAT TTA GAA TTT
Phe Tyr Gly Asn Lys Ser Ser Glu Pro Val Gln Asn Leu Glu Phe

3516/375
AAT GGA GAA AAA GTC TAT AGA GCC GTA GCA AAT ACA AAT CTT GCG
Asn Gly Glu Lys Val Tyr Arg Ala Val Ala Asn Thr Asn Leu Ala

3561/390
GTC TGG CCG TCC GCT GTA TAT TCA GGT GTT ACA AAA GTG GAA TTT
Val Trp Pro Ser Ala Val Tyr Ser Gly Val Thr Lys Val Glu Phe

3606/405
AGC CAA TAT AAT GAT CAA ACA GAT GAA GCA AGT ACA CAA ACG TAC
Ser Gln Tyr Asn Asp Gln Thr Asp Glu Ala Ser Thr Gln Thr Tyr

3651/420
GAC TCA AAA AGA AAT GTT GGC GCG GTC AGC TGG GAT TCT ATC GAT
Asp Ser Lys Arg Asn Val Gly Ala Val Ser Trp Asp Ser Ile Asp

3696/435
CAA TTG CCT CCA GAA ACA ACA GAT GAA CCT CTA GAA AAG GGA TAT
Gln Leu Pro Pro Glu Thr Thr Asp Glu Pro Leu Glu Lys Gly Tyr

3741/450
AGC CAT CAA CTC AAT TAT GTA ATG TGC TTT TTA ATG CAG GGT AGT
Ser His Gln Leu Asn Tyr Val Met Cys Phe Leu Met Gln Gly Ser

3786/465
AGA GGA ACA ATC CCA GTG TTA ACT TGG ACA CAT AAA AGT GTA GAC
Arg Gly Thr Ile Pro Val Leu Thr Trp Thr His Lys Ser Val Asp

3831/480
TTT TTT AAC ATG ATT GAT TCG AAA AAA ATT ACA CAA CTT CCG TTA
Phe Phe Asn Met Ile Asp Ser Lys Lys Ile Thr Gln Leu Pro Leu
```

FIG. 17d

```
                                                                3876/495
GTA AAG GCA TAT AAG TTA CAA TCT GGT GCT TCC GTT GTC GCA GGT
Val Lys Ala Tyr Lys Leu Gln Ser Gly Ala Ser Val Val Ala Gly

3921/510
CCT AGG TTT ACA GGA GGA GAT ATC ATT CAA TGC ACA GAA AAT GGA
Pro Arg Phe Thr Gly Gly Asp Ile Ile Gln Cys Thr Glu Asn Gly

3966/525
AGT GCG GCA ACT ATT TAC GTT ACA CCG GAT GTG TCG TAC TCT CAA
Ser Ala Ala Thr Ile Tyr Val Thr Pro Asp Val Ser Tyr Ser Gln

4011/540
AAA TAT CGA GCT AGA ATT CAT TAT GCT TCT ACA TCT CAG ATA ACA
Lys Tyr Arg Ala Arg Ile His Tyr Ala Ser Thr Ser Gln Ile Thr

4056/555
TTT ACA CTC AGT TTA GAC GGG GCA CCA TTT AAT CAA TAC TAT TTC
Phe Thr Leu Ser Leu Asp Gly Ala Pro Phe Asn Gln Tyr Tyr Phe

4101/570
GAT AAA ACG ATA AAT AAA GGA GAC ACA TTA ACG TAT AAT TCA TTT
Asp Lys Thr Ile Asn Lys Gly Asp Thr Leu Thr Tyr Asn Ser Phe

4146/585
AAT TTA GCA AGT TTC AGC ACA CCA TTC GAA TTA TCA GGG AAT AAC
Asn Leu Ala Ser Phe Ser Thr Pro Phe Glu Leu Ser Gly Asn Asn

4191/600
TTA CAA ATA GGC GTC ACA GGA TTA AGT GCT GGA GAT AAA GTT TAT
Leu Gln Ile Gly Val Thr Gly Leu Ser Ala Gly Asp Lys Val Tyr

4236/615
ATA GAC AAA ATT GAA TTg ggg atc gat cct cta gag tcg acc tgc
Ile Asp Lys Ile Glu Leu Gly Ile Asp Pro Leu Glu Ser Thr Cys 4281/630
agc cca agc tTC GAG TGC CAG GAC GAC ACG GAC GAG TGC CAG GTA
Ser Pro Ser Phe Glu Cys Gln Asp Asp Thr Asp Glu Cys Gln Val 4326/645
TAC ATT TTG GAC GCT GAG GGC AAC CCC ATC AAC GTG ACC GTG GAC
Tyr Ile Leu Asp Ala Glu Gly Asn Pro Ile Asn Val Thr Val Asp
```

FIG. 17e

```
                                                                   4371/660
ACT GTG CTT CAT CGA GAC GGC GTG AGT ATG ATT CTC AAA CAA AAG
Thr Val Leu His Arg Asp Gly Val Ser Met Ile Leu Lys Gln Lys

4416/675
TCT ACG TTC ACC ACG CGC CAA ATA AAA GCT GCG TGT CTG CTC ATT
Ser Thr Phe Thr Thr Arg Gln Ile Lys Ala Ala Cys Leu Leu Ile

4461/690
AAA GAT GAC AAA AAT AAC CCC GAG TCG GTG ACA CGC GAA CAC TGT
Lys Asp Asp Lys Asn Asn Pro Glu Ser Val Thr Arg Glu His Cys

4506/705
TTG ATT GAC AAT GAT ATA TAT GAT CTT TCT AAA AAC ACG TGG AAC
Leu Ile Asp Asn Asp Ile Tyr Asp Leu Ser Lys Asn Thr Trp Asn

4551/720
TGC AAG TTT AAC AGA TGC ATT AAA CGC AAA GTC GAG CAC CGA GTC
Cys Lys Phe Asn Arg Cys Ile Lys Arg Lys Val Glu His Arg Val

4596/735
AAG AAG CGG CCG CCC ACT TGG CGC CAC AAC GTT AGA GCC AAG TAC
Lys Lys Arg Pro Pro Thr Trp Arg His Asn Val Arg Ala Lys Tyr

4641/750
ACA GAG GGA GAC ACT GCC ACC AAA GGC GAC CTG ATG CAT ATT CAA
Thr Glu Gly Asp Thr Ala Thr Lys Gly Asp Leu Met His Ile Gln

4686/765
GAG GAG CTG ATG TAC GAA AAC GAT TTG CTG AAA ATG AAC ATT GAG
Glu Glu Leu Met Tyr Glu Asn Asp Leu Leu Lys Met Asn Ile Glu

4731/780
CTG ATG CAT GCG CAC ATC AAC AAG CTA AAC AAT ATG CTG CAC GAC
Leu Met His Ala His Ile Asn Lys Leu Asn Asn Met Leu His Asp

4776/795
CTG ATA GTC TCC GTG GCC AAG GTG GAC GAG CGT TTG ATT GGC AAT
Leu Ile Val Ser Val Ala Lys Val Asp Glu Arg Leu Ile Gly Asn

4821/810
CTC ATG AAC AAC TCT GTT TCT TCA ACA TTT TTG TCG GAC GAC ACG
Leu Met Asn Asn Ser Val Ser Ser Thr Phe Leu Ser Asp Asp Thr
```

FIG. 17f

```
                                                          4866/825
TTT TTG CTG ATG CCG TGC ACC AAT CCG CCG GCA CAC ACC AGT AAT
Phe Leu Leu Met Pro Cys Thr Asn Pro Pro Ala His Thr Ser Asn

4911/840
TGC TAC AAC AAC AGC ATC TAC AAA GAA GGG CGT TGG GTG GCC AAC
Cys Tyr Asn Asn Ser Ile Tyr Lys Glu Gly Arg Trp Val Ala Asn

4956/855
ACG GAC TCG TCG CAA TGC ATA GAT TTT AGC AAC TAC AAG GAA CTA
Thr Asp Ser Ser Gln Cys Ile Asp Phe Ser Asn Tyr Lys Glu Leu

5001/870
GCA ATT GAC GAC GAC GTC GAG TTT TGG ATC CCG ACC ATC GGC AAC
Ala Ile Asp Asp Asp Val Glu Phe Trp Ile Pro Thr Ile Gly Asn

5046/885
ACG ACC TAT CAC GAC AGT TGG AAA GAT GCC AGC GGC TGG TCG TTT
Thr Thr Tyr His Asp Ser Trp Lys Asp Ala Ser Gly Trp Ser Phe

5091/900
ATT GCC CAA CAA AAA AGC AAC CTC ATA ACC ACC ATG GAG AAC ACC
Ile Ala Gln Gln Lys Ser Asn Leu Ile Thr Thr Met Glu Asn Thr

5136/915
AAG TTT GGC GGC GTC GGC ACC AGT CTG AGC GAC ATC ACT TCC ATG
Lys Phe Gly Gly Val Gly Thr Ser Leu Ser Asp Ile Thr Ser Met

5181/930
GCT GAA GGC GAA TTG GCC GCT AAA TTG ACT TCG TTC ATG TTT GGT
Ala Glu Gly Glu Leu Ala Ala Lys Leu Thr Ser Phe Met Phe Gly

5226/945
CAT GTA GTT AAC TTT GTA ATT ATA TTA ATT GTG ATT TTA TTT TTG
His Val Val Asn Phe Val Ile Ile Leu Ile Val Ile Leu Phe Leu

5262/956
TAC TGT ATG ATT AGA AAC CGT AAT AGA CAA TAT TAA
Tyr Cys Met Ile Arg Asn Arg Asn Arg Gln Tyr OCH
```

FIG. 18a pFAC13 = 104 kD fusion protein sequence pT7-7/SX12/AccI(gp64) [2392 to 5136] -> 1-Phase Translation DNA sequence 5415 b.p. AAATCAATCTAA...AACATGAGAATT  Circular

```
2392/1                                                    2436/15
atg gct aga att cgc gcc cgg gga tcc tct aga gtc gat cga cct
Met Ala Arg Ile Arg Ala Arg Gly Ser Ser Arg Val Asp Arg Pro 2481/30
gCA GAT AAT AAT ACG GAA GCA CTA GAT AGC TCT ACA ACA AAA GAT
Ala Asp Asn Asn Thr Glu Ala Leu Asp Ser Ser Thr Thr Lys Asp 2526/45
GTC ATT CAA AAA GGC ATT TCC GTA GTA GGT GAT CTC CTA GGC GTA
Val Ile Gln Lys Gly Ile Ser Val Val Gly Asp Leu Leu Gly Val 2571/60
GTA GGT TTC CCG TTT GGT GGA GCG CTT GTT TCG TTT TAT ACA AAC
Val Gly Phe Pro Phe Gly Gly Ala Leu Val Ser Phe Tyr Thr Asn 2616/75
TTT TTA AAT ACT ATT TGG CCA AGT GAA GAC CCG TGG AAG GCT TTT
Phe Leu Asn Thr Ile Trp Pro Ser Glu Asp Pro Trp Lys Ala Phe 2661/90
ATG GAA CAA GTA GAA GCA TTG ATG GAT CAG AAA ATA GCT GAT TAT
Met Glu Gln Val Glu Ala Leu Met Asp Gln Lys Ile Ala Asp Tyr 2706/105
GCA AAA AAT AAA GCT CTT GCA GAG TTA CAG GGC CTT CAA AAT AAT
Ala Lys Asn Lys Ala Leu Ala Glu Leu Gln Gly Leu Gln Asn Asn 2751/120
GTC GAA GAT TAT GTG AGT GCA TTG AGT TCA TGG CAA AAA AAT CCT
Val Glu Asp Tyr Val Ser Ala Leu Ser Ser Trp Gln Lys Asn Pro 2796/135
GTG AGT TCA CGA AAT CCA CAT AGC CAG GGG CGG ATA AGA GAG CTG
Val Ser Ser Arg Asn Pro His Ser Gln Gly Arg Ile Arg Glu Leu 2841/150
TTT TCT CAA GCA GAA AGT CAT TTT CGT AAT TCA ATG CCT TCG TTT
Phe Ser Gln Ala Glu Ser His Phe Arg Asn Ser Met Pro Ser Phe
```

FIG. 18b

```
                                                              2886/165
GCA ATT TCT GGA TAC GAG GTT CTA TTT CTA ACA ACA TAT GCA CAA
Ala Ile Ser Gly Tyr Glu Val Leu Phe Leu Thr Thr Tyr Ala Gln

2931/180
GCT GCC AAC ACA CAT TTA TTT TTA CTA AAA GAC GCT CAA ATT TAT
Ala Ala Asn Thr His Leu Phe Leu Leu Lys Asp Ala Gln Ile Tyr

2976/195
GGA GAA GAA TGG GGA TAC GAA AAA GAA GAT ATT GCT GAA TTT TAT
Gly Glu Glu Trp Gly Tyr Glu Lys Glu Asp Ile Ala Glu Phe Tyr

3021/210
AAA AGA CAA CTA AAA CTT ACG CAA GAA TAT ACT GAC CAT TGT GTC
Lys Arg Gln Leu Lys Leu Thr Gln Glu Tyr Thr Asp His Cys Val

3066/225
AAA TGG TAT AAT GTT GGA TTA GAT AAA TTA AGA GGT TCA TCT TAT
Lys Trp Tyr Asn Val Gly Leu Asp Lys Leu Arg Gly Ser Ser Tyr

3111/240
GAA TCT TGG GTA AAC TTT AAC CGT TAT CGC AGA GAG ATG ACA TTA
Glu Ser Trp Val Asn Phe Asn Arg Tyr Arg Arg Glu Met Thr Leu

3156/255
ACA GTA TTA GAT TTA ATT GCA CTA TTT CCA TTG TAT GAT GTT CGG
Thr Val Leu Asp Leu Ile Ala Leu Phe Pro Leu Tyr Asp Val Arg

3201/270
CTA TAC CCA AAA GAA GTT AAA ACC GAA TTA ACA AGA GAC GTT TTA
Leu Tyr Pro Lys Glu Val Lys Thr Glu Leu Thr Arg Asp Val Leu

3246/285
ACA GAT CCA ATT GTC GGA GTC AAC AAC CTT AGG GGC TAT GGA ACA
Thr Asp Pro Ile Val Gly Val Asn Asn Leu Arg Gly Tyr Gly Thr

3291/300
ACC TTC TCT AAT ATA GAA AAT TAT ATT CGA AAA CCA CAT CTA TTT
Thr Phe Ser Asn Ile Glu Asn Tyr Ile Arg Lys Pro His Leu Phe

3336/315
GAC TAT CTG CAT AGA ATT CAA TTT CAC ACG CGG TTC CAA CCA GGA
Asp Tyr Leu His Arg Ile Gln Phe His Thr Arg Phe Gln Pro Gly
```

FIG. 18c

```
                                                        3381/330
TAT TAT GGA AAT GAC TCT TTC AAT TAT TGG TCC GGT AAT TAT GTT
Tyr Tyr Gly Asn Asp Ser Phe Asn Tyr Trp Ser Gly Asn Tyr Val

3426/345
TCA ACT AGA CCA AGC ATA GGA TCA AAT GAT ATA ATC ACA TCT CCA
Ser Thr Arg Pro Ser Ile Gly Ser Asn Asp Ile Ile Thr Ser Pro

3471/360
TTC TAT GGA AAT AAA TCC AGT GAA CCT GTA CAA AAT TTA GAA TTT
Phe Tyr Gly Asn Lys Ser Ser Glu Pro Val Gln Asn Leu Glu Phe

3516/375
AAT GGA GAA AAA GTC TAT AGA GCC GTA GCA AAT ACA AAT CTT GCG
Asn Gly Glu Lys Val Tyr Arg Ala Val Ala Asn Thr Asn Leu Ala

3561/390
GTC TGG CCG TCC GCT GTA TAT TCA GGT GTT ACA AAA GTG GAA TTT
Val Trp Pro Ser Ala Val Tyr Ser Gly Val Thr Lys Val Glu Phe

3606/405
AGC CAA TAT AAT GAT CAA ACA GAT GAA GCA AGT ACA CAA ACG TAC
Ser Gln Tyr Asn Asp Gln Thr Asp Glu Ala Ser Thr Gln Thr Tyr

3651/420
GAC TCA AAA AGA AAT GTT GGC GCG GTC AGC TGG GAT TCT ATC GAT
Asp Ser Lys Arg Asn Val Gly Ala Val Ser Trp Asp Ser Ile Asp

3696/435
CAA TTG CCT CCA GAA ACA ACA GAT GAA CCT CTA GAA AAG GGA TAT
Gln Leu Pro Pro Glu Thr Thr Asp Glu Pro Leu Glu Lys Gly Tyr

3741/450
AGC CAT CAA CTC AAT TAT GTA ATG TGC TTT TTA ATG CAG GGT AGT
Ser His Gln Leu Asn Tyr Val Met Cys Phe Leu Met Gln Gly Ser

3786/465
AGA GGA ACA ATC CCA GTG TTA ACT TGG ACA CAT AAA AGT GTA GAC
Arg Gly Thr Ile Pro Val Leu Thr Trp Thr His Lys Ser Val Asp

3831/480
TTT TTT AAC ATG ATT GAT TCG AAA AAA ATT ACA CAA CTT CCG TTA
Phe Phe Asn Met Ile Asp Ser Lys Lys Ile Thr Gln Leu Pro Leu
```

FIG. 18d

```
                                                                  3876/495
GTA AAG GCA TAT AAG TTA CAA TCT GGT GCT TCC GTT GTC GCA GGT
Val Lys Ala Tyr Lys Leu Gln Ser Gly Ala Ser Val Val Ala Gly

3921/510
CCT AGG TTT ACA GGA GGA GAT ATC ATT CAA TGC ACA GAA AAT GGA
Pro Arg Phe Thr Gly Gly Asp Ile Ile Gln Cys Thr Glu Asn Gly
                                                                  3966/525
AGT GCG GCA ACT ATT TAC GTT ACA CCG GAT GTG TCG TAC TCT CAA
Ser Ala Ala Thr Ile Tyr Val Thr Pro Asp Val Ser Tyr Ser Gln

4011/540
AAA TAT CGA GCT AGA ATT CAT TAT GCT TCT ACA TCT CAG ATA ACA
Lys Tyr Arg Ala Arg Ile His Tyr Ala Ser Thr Ser Gln Ile Thr

4056/555
TTT ACA CTC AGT TTA GAC GGG GCA CCA TTT AAT CAA TAC TAT TTC
Phe Thr Leu Ser Leu Asp Gly Ala Pro Phe Asn Gln Tyr Tyr Phe

4101/570
GAT AAA ACG ATA AAT AAA GGA GAC ACA TTA ACG TAT AAT TCA TTT
Asp Lys Thr Ile Asn Lys Gly Asp Thr Leu Thr Tyr Asn Ser Phe

4146/585
AAT TTA GCA AGT TTC AGC ACA CCA TTC GAA TTA TCA GGG AAT AAC
Asn Leu Ala Ser Phe Ser Thr Pro Phe Glu Leu Ser Gly Asn Asn

4191/600
TTA CAA ATA GGC GTC ACA GGA TTA AGT GCT GGA GAT AAA GTT TAT
Leu Gln Ile Gly Val Thr Gly Leu Ser Ala Gly Asp Lys Val Tyr

4236/615
ATA GAC AAA ATT GAA TTg ggg atc gat cct cta gag tcg acc tgc
Ile Asp Lys Ile Glu Leu Gly Ile Asp Pro Leu Glu Ser Thr Cys 4281/630
agc cca agc tCT ACG TTC ACC ACG CGC CAA ATA AAA GCT GCG TGT
Ser Pro Ser Ser Thr Phe Thr Thr Arg Gln Ile Lys Ala Ala Cys 4326/645
CTG CTC ATT AAA GAT GAC AAA AAT AAC CCC GAG TCG GTG ACA CGC
Leu Leu Ile Lys Asp Asp Lys Asn Asn Pro Glu Ser Val Thr Arg 4371/660
GAA CAC TGT TTG ATT GAC AAT GAT ATA TAT GAT CTT TCT AAA AAC
Glu His Cys Leu Ile Asp Asn Asp Ile Tyr Asp Leu Ser Lys Asn
```

FIG. 18e

```
                                                                    4416/675
ACG TGG AAC TGC AAG TTT AAC AGA TGC ATT AAA CGC AAA GTC GAG
Thr Trp Asn Cys Lys Phe Asn Arg Cys Ile Lys Arg Lys Val Glu

4461/690
CAC CGA GTC AAG AAG CGG CCG CCC ACT TGG CGC CAC AAC GTT AGA
His Arg Val Lys Lys Arg Pro Pro Thr Trp Arg His Asn Val Arg
                                                                    4506/705
GCC AAG TAC ACA GAG GGA GAC ACT GCC ACC AAA GGC GAC CTG ATG
Ala Lys Tyr Thr Glu Gly Asp Thr Ala Thr Lys Gly Asp Leu Met

4551/720
CAT ATT CAA GAG GAG CTG ATG TAC GAA AAC GAT TTG CTG AAA ATG
His Ile Gln Glu Glu Leu Met Tyr Glu Asn Asp Leu Leu Lys Met

4596/735
AAC ATT GAG CTG ATG CAT GCG CAC ATC AAC AAG CTA AAC AAT ATG
Asn Ile Glu Leu Met His Ala His Ile Asn Lys Leu Asn Asn Met

4641/750
CTG CAC GAC CTG ATA GTC TCC GTG GCC AAG GTG GAC GAG CGT TTG
Leu His Asp Leu Ile Val Ser Val Ala Lys Val Asp Glu Arg Leu

4686/765
ATT GGC AAT CTC ATG AAC AAC TCT GTT TCT TCA ACA TTT TTG TCG
Ile Gly Asn Leu Met Asn Asn Ser Val Ser Ser Thr Phe Leu Ser

4731/780
GAC GAC ACG TTT TTG CTG ATG CCG TGC ACC AAT CCG CCG GCA CAC
Asp Asp Thr Phe Leu Leu Met Pro Cys Thr Asn Pro Pro Ala His

4776/795
ACC AGT AAT TGC TAC AAC AAC AGC ATC TAC AAA GAA GGG CGT TGG
Thr Ser Asn Cys Tyr Asn Asn Ser Ile Tyr Lys Glu Gly Arg Trp

4821/810
GTG GCC AAC ACG GAC TCG TCG CAA TGC ATA GAT TTT AGC AAC TAC
Val Ala Asn Thr Asp Ser Ser Gln Cys Ile Asp Phe Ser Asn Tyr

4866/835
AAG GAA CTA GCA ATT GAC GAC GAC GTC GAG TTT TGG ATC CCG ACC
Lys Glu Leu Ala Ile Asp Asp Asp Val Glu Phe Trp Ile Pro Thr
```

FIG. 18f

```
                                                          4911/840
ATC GGC AAC ACG ACC TAT CAC GAC AGT TGG AAA GAT GCC AGC GGC
Ile Gly Asn Thr Thr Tyr His Asp Ser Trp Lys Asp Ala Ser Gly

4956/855
TGG TCG TTT ATT GCC CAA CAA AAA AGC AAC CTC ATA ACC ACC ATG
Trp Ser Phe Ile Ala Gln Gln Lys Ser Asn Leu Ile Thr Thr Met

5001/870
GAG AAC ACC AAG TTT GGC GGC GTC GGC ACC AGT CTG AGC GAC ATC
Glu Asn Thr Lys Phe Gly Gly Val Gly Thr Ser Leu Ser Asp Ile

5046/885
ACT TCC ATG GCT GAA GGC GAA TTG GCC GCT AAA TTG ACT TCG TTC
Thr Ser Met Ala Glu Gly Glu Leu Ala Ala Lys Leu Thr Ser Phe

5091/900
ATG TTT GGT CAT GTA GTT AAC TTT GTA ATT ATA TTA ATT GTG ATT
Met Phe Gly His Val Val Asn Phe Val Ile Ile Leu Ile Val Ile

5136/914
TTA TTT TTG TAC TGT ATG ATT AGA AAC CGT AAT AGA CAA TAT TAA
Leu Phe Leu Tyr Cys Met Ile Arg Asn Arg Asn Arg Gln Tyr OCH
```

FIG. 21a

PG14 72kDa+25 kDa (end) -> List

DNA sequence 2802 b.p. TTTAAAATAAAA...ATAAAACAATCT linear

```
   1 TTTAAAATAA AAAAATTCAA TAAAAGGTGG AATGAATTAT
     ATGGAAGATA GTTCTTTAGA TACTTTAAGT ATAGTTAATG   80
  81 AAACAGACTT TCCATTATAT AATAATTATA CCGAACCTAC
     TATTGCGCCA GCATTAATAG CAGTAGCTCC CATCGCACAA  160
 161 TATCTTGCAA CAGCTATAGG GAAATGGGCG GCAAAGGCAG
     CATTTCAAA AGTACTATCA CTTATATTCC CAGGTTCTCA  240
 241 ACCTGCTACT ATGGAAAAAG TTCGTACAGA AGTGGAAACA
     CTTATAAATC AAAAATTAAG CCAAGATCGA GTCAATATAT  320
 321 TAAACGCAGA ATATAGGGGG ATTATTGAGG TTAGTGATGT
     ATTTGATGCG TATATTAAAC AACCAGGTTT TACCCCTGCA  400
 401 ACAGCCAAGG GTTATTTTCT AAATCTAAGT GGTGCTATAA
     TACAACGATT ACCTCAATTT GAGGTTCAAA CATATGAAGG  480
 481 AGTATCTATA GCACTTTTTA CTCAAATGTG TACACTTCAT
     TTAACTTTAT TAAAAGACGG AATCCTAGCA GGGAGTGCAT  560
 561 GGGGATTTAC TCAAGCTGAT GTAGATTCAT TTATAAAATT
     ATTTAATCAA AAAGTATTAG ATTACAGGAC CAGATTAATG  640
 641 AGAATGTACA CAGAAGAGTT CGGAAGATTG TGTAAAGTCA
     GTCTTAAAGA TGGATTGACG TTCCGGAATA TGTGTAATTT  720
 721 ATATGTGTTT CCATTGCTG AAGCCTGGTC TTTAATGAGA
     TATGAAGGAT TAAAATTACA AAGCTCTCTA TCATTATGGG  800
 801 ATTATGTTGG TGTCTCAATT CCTGTAAATT ATAATGAATG
     GGGAGGACTA GTTTATAAGT TATTAATGGG GGAAGTTAAT  880
 881 CAAAGATTAA CAACTGTTAA ATTTAATTAT TCTTTCACTA
     ATGAACCAGC TGATATACCA GCAAGAGAAA ATATTCGTGG  960
 961 CGTCCATCCT ATATACGATC CTAGTTCTGG GCTTACAGGA
     TGGATAGGAA ACGGAAGAAC AAACAATTTT AATTTTGCTG 1040
1041 ATAACAATGG CAATGAAATT ATGGAAGTTA GAACACAAAC
     TTTTTATCAA AATCCAAATA ATGAGCCTAT AGCGCCTAGA 1120
1121 GATATTATAA ATCAAATTTT AACTGCGCCA GCACCAGCAG
     ACCTATTTTT TAAAAATGCA GATATAAATG TAAAGTTCAC 1200
1201 ACAGTGGTTT CAGTCTACTC TATATGGGTG GAACATTAAA
     CTCGGTACAC AAACGGTTTT AAGTAGTAGA ACCGGAACAA 1280
1281 TACCACCAAA TTATTTAGCA TATGATGGAT ATTATATTCG
     TGCTATTTCA GCTTGCCCAA GAGGAGTCTC ACTTGCATAT 1360
1361 AATCACGATC TTACAACACT AACATATAAT AGAATAGAGT
     ATGATTCACC TACTACAGAA AATATTATTG TAGGGTTTGC 1440
1441 ACCAGATAAT ACTAAGGACT TTATTCTAA AAAATCTCAC
     TATTTAAGTG AAACGAATGA TAGTTATGTA ATTCCTGCTC 1520
1521 TGCAATTTGC TGAAGTTTCA GATAGATCAT TTTAGAAGA
```

FIG. 21b

```
     TACGCCAGAT CAAGCAACAG ACGGCAGTAT TAAATTTGCA 1600
1601 CGTACTTTCA TTAGTAATGA AGCTAAGTAC TCTATTAGAC
     TAAACACCGG GTTTAATACG GCAACTAGAT ATAAATTAAT 1680
1681 TATCAGGGTA AGAGTACCTT ATCGCTTACC TGCTGGAATA
     CGGGTACAAT CTCAGAATTC GGGAAATAAT AGAATGCTAG 1760
1761 GCAGTTTTAC TGCAAATGCT AATCCAGAAT GGGTGGATTT
     TGTCACAGAT GCATTTACAT TTAACGATTT AGGGATTACA 1840
1841 ACTTCAAGTA CAAATGCTTT ATTTAGTATT TCTTCAGATA
     GTTTAAATTC TGGAGAAGAG TGGTATTTAT CGCAGTTGTT 1920
1921 TTTAGTAAAA GAATCGGggg ctgcaggaat tcgatatcaa
     gcttatcgat accgtcgaCG TGTTGAGGAT CCAAATGAAA 2000
2001 TCAATAATCT TCTTTCTATT AACGAAATTG ATAATCCGAA
     TTATATATTG CAAGCAATTA TGTTAGCAAA TGCATTTCAA 2080
2081 AATGCATTAG TTCCCACTTC TACAGATTTT GGTGATGCCC
     TACGCTTTAG TATGGCAAAA GGTTTAGAAA TCGCAAACAC 2160
2161 AATTACACCG ATGCGTGCTG TAGTGAGTTA TGTTGATCAA
     AATGTAACTC AAACGAATAA CCAAGTAAGT GTTATGATTA 2240
2241 ATAAAGTCTT AGAAGTGTTA AAAACTGTAT TAGGAGTTGC
     ATTAAGTGGA TCTGTAATAG ATCAATTAAC TGCAGCAGTT 2320
2321 ACAAATACGT TTACAAATTT AAATACTCAA AAAAATGAAG
     CATGGATTTT CTGGGGCAAG GAAACTGCTA ATCAAACAAA 2400
2401 TTACACATAC AATGTCCTGT TTGCAATCCA AAATGCCCAA
     ACTGGTGGCG TTATGTATTG TGTACCAGTT GGTTTTGAAA 2480
2481 TTAAAGTATC AGCAGTAAAG GAACAAGTTT TATTTTTCAC
     AATTCAAGAT TCTGCGAGCT ACAATGTTAA CATCCAATCT 2560
2561 TTGAAATTTG CACAACCATT AGTTAGCTCA AGTCAGTATC
     CAATTGCAGA TCTTACTAGC GCTATTAATG GAACCCTCTA 2640
2641 ATCTTAGTAG CTATATTTAT TAAAGATGGT AATATCACAA
     GTATAAATAC TTGTGGTATT ACCTACCATT CTTAAATTAT 2720
2721 ATCCAAAATC ATGCGTTAAT CTACATTCCC CTTTCTCTAA
     AATTTGTTCT TCACACATCC ACATTTTCG ATAAAACAAT 2800
2801 CT                                           2802
```

FIG.22a

PG 14 72kDa+27 kDa (end) -> List

DNA sequence 2901 b.p. TTTAAAATAAAA...ATAAAACAATCT linear

```
   1 TTTAAAATAA AAAAATTCAA TAAAAGGTGG AATGAATTAT
     ATGGAAGATA GTTCTTTAGA TACTTTAAGT ATAGTTAATG   80
  81 AAACAGACTT TCCATTATAT AATAATTATA CCGAACCTAC
     TATTGCGCCA GCATTAATAG CAGTAGCTCC CATCGCACAA  160
 161 TATCTTGCAA CAGCTATAGG GAAATGGGCG GCAAAGGCAG
     CATTTTCAAA AGTACTATCA CTTATATTCC CAGGTTCTCA  240
 241 ACCTGCTACT ATGGAAAAAG TTCGTACAGA AGTGGAAACA
     CTTATAAATC AAAAATTAAG CCAAGATCGA GTCAATATAT  320
 321 TAAACGCAGA ATATAGGGGG ATTATTGAGG TTAGTGATGT
     ATTTGATGCG TATATTAAAC AACCAGGTTT TACCCCTGCA  400
 401 ACAGCCAAGG GTTATTTTCT AAATCTAAGT GGTGCTATAA
     TACAACGATT ACCTCAATTT GAGGTTCAAA CATATGAAGG  480
 481 AGTATCTATA GCACTTTTTA CTCAAATGTG TACACTTCAT
     TTAACTTTAT TAAAGACGG AATCCTAGCA GGGAGTGCAT   560
 561 GGGGATTTAC TCAAGCTGAT GTAGATTCAT TTATAAAATT
     ATTTAATCAA AAAGTATTAG ATTACAGGAC CAGATTAATG  640
 641 AGAATGTACA CAGAAGAGTT CGGAAGATTG TGTAAAGTCA
     GTCTTAAAGA TGGATTGACG TTCGGAATA TGTGTAATTT    720
 721 ATATGTGTTT CCATTTGCTG AAGCCTGGTC TTTAATGAGA
     TATGAAGGAT TAAAATTACA AAGCTCTCTA TCATTATGGG  800
 801 ATTATGTTGG TGTCTCAATT CCTGTAAATT ATAATGAATG
     GGGAGGACTA GTTTATAAGT TATTAATGGG GGAAGTTAAT  880
 881 CAAAGATTAA CAACTGTTAA ATTTAATTAT TCTTTCACTA
     ATGAACCAGC TGATATACCA GCAAGAGAAA ATATTCGTGG  960
 961 CGTCCATCCT ATATACGATC CTAGTTCTGG GCTTACAGGA
     TGGATAGGAA ACGGAAGAAC AAACAATTTT AATTTTGCTG 1040
1041 ATAACAATGG CAATGAAATT ATGGAAGTTA GAACACAAAC
     TTTTATCAA AATCCAAATA ATGAGCCTAT AGCGCCTAGA  1120
1121 GATATTATAA ATCAAATTTT AACTGCGCCA GCACCAGCAG
     ACCTATTTTT TAAAAATGCA GATATAAATG TAAAGTTCAC  1200
1201 ACAGTGGTTT CAGTCTACTC TATATGGGTG GAACATTAAA
     CTCGGTACAC AAACGGTTTT AAGTAGTAGA ACCGGAACAA  1280
1281 TACCACCAAA TTATTTAGCA TATGATGGAT ATTATATTCG
     TGCTATTTCA GCTTGCCCAA GAGGAGTCTC ACTTGCATAT  1360
1361 AATCACGATC TTACAACACT AACATATAAT AGAATAGAGT
     ATGATTCACC TACTACAGAA AATATTATTG TAGGGTTTGC  1440
1441 ACCAGATAAT ACTAAGGACT TTATTCTAA AAAATCTCAC
     TATTTAAGTG AAACGAATGA TAGTTATGTA ATTCCTGCTC  1520
```

FIG. 22b

```
1521 TGCAATTTGC TGAAGTTTCA GATAGATCAT TTTTAGAAGA
     TACGCCAGAT CAAGCAACAG ACGGCAGTAT TAAATTTGCA 1600
1601 CGTACTTTCA TTAGTAATGA AGCTAAGTAC TCTATTAGAC
     TAAACACCGG GTTAATACG GCAACTAGAT ATAAATTAAT 1680
1681 TATCAGGGTA AGAGTACCTT ATCGCTTACC TGCTGGAATA
     CGGGTACAAT CTCAGAATTC GGGAAATAAT AGAATGCTAG 1760
1761 GCAGTTTTAC TGCAAATGCT AATCCAGAAT GGGTGGATTT
     TGTCACAGAT GCATTACAT TTAACGATTT AGGGATTACA 1840
1841 ACTTCAAGTA CAAATGCTTT ATTTAGTATT TCTTCAGATA
     GTTTAAATTC TGGAGAAGAG TGGTATTTAT CGCAGTTGTT 1920
1921 TTTAGTAAAA GAATCGGggg ctgcaggaat tcgatCCACT
     ATTCTAATTA ACTTAAGGAG TTGTTTATTT ATGGAAAATT 2000
2001 TAAATCATTG TCCATTAGAA GATATAAAGG TAAATCCATG
     GAAAACCCCT CAATCAACAG CAAGGGTTAT TACATTACGT 2080
2081 GTTGAGGATC CAAATGAAAT CAATAATCTT CTTTCTATTA
     ACGAAATTGA TAATCCGAAT TATATATTGC AAGCAATTAT 2160
2161 GTTAGCAAAT GCATTTCAAA ATGCATTAGT TCCCACTTCT
     ACAGATTTTG GTGATGCCCT ACGCTTTAGT ATGGCAAAAG 2240
2241 GTTTAGAAAT CGCAAACACA ATTACACCGA TGCGTGCTGT
     AGTGAGTTAT GTTGATCAAA ATGTAACTCA AACGAATAAC 2320
2321 CAAGTAAGTG TTATGATTAA TAAAGTCTTA GAAGTGTTAA
     AAACTGTATT AGGAGTTGCA TTAAGTGGAT CTGTAATAGA 2400
2401 TCAATTAACT GCAGCAGTTA CAAATACGTT TACAAATTTA
     AATACTCAAA AAAATGAAGC ATGGATTTTC TGGGGCAAGG 2480
2481 AAACTGCTAA TCAAACAAAT TACACATACA ATGTCCTGTT
     TGCAATCCAA AATGCCCAAA CTGGTGGCGT TATGTATTGT 2560
2561 GTACCAGTTG GTTTTGAAAT TAAAGTATCA GCAGTAAAGG
     AACAAGTTTT ATTTTCACA ATTCAAGATT CTGCGAGCTA 2640
2641 CAATGTTAAC ATCCAATCTT TGAAATTTGC ACAACCATTA
     GTTAGCTCAA GTCAGTATCC AATTGCAGAT CTTACTAGCG 2720
2721 CTATTAATGG AACCCTCTAA TCTTAGTAGC TATATTTATT
     AAAGATGGTA ATATCACAAG TATAAATACT TGTGGTATTA 2800
2801 CCTACCATTC TTAAATTATA TCCAAAATCA TGCGTTAATC
     TACATTCCCC TTTCTCTAAA ATTTGTTCTT CACACATCCA 2880
2881 CATTTTTCGA TAAAACAATC T                        2901
```

FIG. 22c

```
                                                             5046/885
                                          GAG GGA GAC ACT GCC
                                          Glu Gly Asp Thr Ala

5091/900
ACC AAA GGC GAC CTG ATG CAT ATT CAA GAG GAG CTG ATG TAC GAA
Thr Lys Gly Asp Leu Met His Ile Gln Glu Glu Leu Met Tyr Glu

5136/915
AAC GAT TTG CTG AAA ATG AAC ATT GAG CTG ATG CAT GCG CAC ATC
Asn Asp Leu Leu Lys Met Asn Ile Glu Leu Met His Ala His Ile

5181/930
AAC AAG CTA AAC AAT ATG CTG CAC GAC CTG ATA GTC TCC GTG GCC
Asn Lys Leu Asn Asn Met Leu His Asp Leu Ile Val Ser Val Ala

5226/945
AAG GTG GAC GAG CGT TTG ATT GGC AAT CTC ATG AAC AAC TCT GTT
Lys Val Asp Glu Arg Leu Ile Gly Asn Leu Met Asn Asn Ser Val

5271/960
TCT TCA ACA TTT TTG TCG GAC GAC ACG TTT TTG CTG ATG CCG TGC
Ser Ser Thr Phe Leu Ser Asp Asp Thr Phe Leu Leu Met Pro Cys

5316/975
ACC AAT CCG CCG GCA CAC ACC AGT AAT TGC TAC AAC AAC AGC ATC
Thr Asn Pro Pro Ala His Thr Ser Asn Cys Tyr Asn Asn Ser Ile

5361/990
TAC AAA GAA GGG CGT TGG GTG GCC AAC ACG GAC TCG TCG CAA TGC
Tyr Lys Glu Gly Arg Trp Val Ala Asn Thr Asp Ser Ser Gln Cys

5406/1005
ATA GAT TTT AGC AAC TAC AAG GAA CTA GCA ATT GAC GAC GAC GTC
Ile Asp Phe Ser Asn Tyr Lys Glu Leu Ala Ile Asp Asp Asp Val

5451/1020
GAG TTT TGG ATC CCG ACC ATC GGC AAC ACG ACC TAT CAC GAC AGT
Glu Phe Trp Ile Pro Thr Ile Gly Asn Thr Thr Tyr His Asp Ser

5496/1035
TGG AAA GAT GCC AGC GGC TGG TCG TTT ATT GCC CAA CAA AAA AGC
Trp Lys Asp Ala Ser Gly Trp Ser Phe Ile Ala Gln Gln Lys Ser

5541/1050
AAC CTC ATA ACC ACC ATG GAG AAC ACC AAG TTT GGC GGC GTC GGC
Asn Leu Ile Thr Thr Met Glu Asn Thr Lys Phe Gly Gly Val Gly
```

FIG. 22d

```
                                                                  5586/1065
ACC AGT CTG AGC GAC ATC ACT TCC ATG GCT GAA GGC GAA TTG GCC
Thr Ser Leu Ser Asp Ile Thr Ser Met Ala Glu Gly Glu Leu Ala

5631/1080
GCT AAA TTG ACT TCG TTC ATG TTT GGT CAT GTA GTT AAC TTT GTA
Ala Lys Leu Thr Ser Phe Met Phe Gly His Val Val Asn Phe Val

5676/1095
ATT ATA TTA ATT GTG ATT TTA TTT TTG TAC TGT ATG ATT AGA AAC
Ile Ile Leu Ile Val Ile Leu Phe Leu Tyr Cys Met Ile Arg Asn

5694/1101
CGT AAT AGA CAA TAT TAA
Arg Asn Arg Gln Tyr OCH
```

METHOD AND MEANS FOR EXTENDING THE HOST RANGE OF INSECTICIDAL PROTEINS

FIELD OF THE INVENTION

This invention relates to the field of recombinant DNA technology. Specifically, the present invention relates to methods and means for extending the host range of insecticidal proteins and/or increasing their toxicity in a certain species. These goals can be achieved by fusing an insecticidal protein with another protein segment capable of interacting with the midgut or hindgut epithelium of immature or adult target insects. The present invention relates to the designing of such new chimeric proteins having extended host range and/or increased toxicity. More particularly, the invention concerns chimeric proteins comprising a first protein segment having insecticidal activity and a second protein segment capable of binding strongly to the midgut or hindgut cell membrane of a target insect (including larval stage of development and mature insects) to which the first protein segment is not efficiently bound. The first protein segment preferably is a crystal protein (δ-endotoxin) of Bacillus thurinoiensis (B. thuringiensis), or a fragment thereof having insecticidal activity, whereas the second protein segment may, for example, be a surface glycoprotein of an insect nuclear polyhedrosis virus. By combining a B. thuringiensis insecticidal crystal protein with another protein segment capable of binding to the midgut or hindgut epithelium of a target insect, the otherwise rather limited host range of B. thuringiensis crystal insecticidal proteins can be substantially increased, and the toxicity can be improved. The invention relates to all means and method associated with the production and use of such chimeric proteins. The invention also includes other methods for increasing the host range and/or improving the toxicity of insecticidal proteins which do not require the construction of such chimeric proteins.

BACKGROUND OF THE INVENTION

For nearly forty years, agriculture, public health agencies and the forestry industry have come to rely more and more on synthetic chemicals for protection against wide variety of pests. However, the use of such broad-spectrum chemical pesticides posed several problems, such as environmental contamination, adverse effects on non-target organisms, residues in food and water, accumulation of chemicals in the food chain and development of resistance in insects due to the repeated use of chemical insecticides. Public concern for environmental quality has led to increased emphasis on alternative safe pest management strategies.

For many years there has been considerable interest in using pathogens, particularly viruses and bacteria that cause disease and show toxicity in insects, as alternatives to synthetic chemicals for controlling insect pests and vectors of various animal and human diseases. At present, probably the best understood, and certainly the commercially most successful biological control agent is a gram-positive soil bacterium, *Bacillus thuringiensis* (*B. thuringiensis*, Bt).

Many *B. thuringiensis* strains with different insect host spectra have been identified. Most of them are active against larvae of certain members of the Lepidoptera, but some show toxicity against a few dipteran or coleopteran species. *B. thuringiensis* has proved to be effective and harmless to the environment owing to its specificity, and therefore, is considered as an alternative to conventional insecticides. Formulations of *B. thuringiensis* spore-crystal mixtures are commercially available. However, the practical use of *B. thuringiensis* as a biological insect control agent is greatly limited by its limited host-range and poor efficacy against many pests.

Several agricultural biotechnology companies are currently devoting their major resources to screening soil samples from different environments all over the world in the hope of getting new isolates of *B. thuringiensis* with increased toxicity and broader or different host range, with very limited success.

Attempts to improve efficacy and host range have failed primarily because so far little effort has been devoted to understanding the molecular basis for the specifity of *B. thuringiensis*.

*B. thuringiensis* is known to produce crystalline inclusions during sporulation. When ingested by the larvae of target insects, these crystalline inclusions are solubilized in the larval midgut, releasing one or more crystal proteins (Cry proteins, also referred to as δ-endotoxins) of 27 to 140 kD exhibiting highly specific insecticidal activity. Experimental evidence shows that most of these crystal proteins are protoxins that are proteolytically converted into smaller toxic polypeptides in the insect midgut. The "activated" toxin interacts with the midgut epithelium cells of susceptible insects. According to a recent model, the toxins induce the formation of small, non-specific pores (0.5 to 1 nm) in the membrane of susceptible cells, resulting in a net influx of ions and an accompanying inflow of water. As a consequence, the cells swell and lyse.

Many insecticidal proteins, such as those of the Cry type produced by *B. thuringiensis*, are limited in their usefulness as insecticides because their host range is rather narrow, typically limited to species of the same genus. According to a recent review by H. Hofte and H. R. Whiteley [*Microbiological Reviews* 53, 242–255 (1989)], nucleotide sequences have been reported in the art for 42 *B. thuringiensis* crystal protein-encoding genes, of which 14 are clearly distinctly different, whereas the rest are identical or only slightly different and thus represent the same gene including its different variants. Hofte and Whiteley provide a detailed characterization of these genes, and propose a nomenclature and classification scheme for the genes and the encoded crystal proteins based on their structure (nucleotide and deduced amino acid sequences) as well as their host range. The specificity of the crystal proteins of *B. thuringiensis* is considered to be determined by hypervariable amino acid regions of these proteins, whereas the toxic moiety of these same proteins is thought to be largely the same and defined in highly conserved regions. For example, Hofte and Whiteley, Supra, compared the deduced amino acid sequence of a wide range of *B. thuringiensis* Cry proteins and show the existence of five highly conserved regions, i.e. regions similar and in many cases of identical amino acid sequence that occur in almost all Cry proteins. Ge et al., *Proc. Natl. Acad. Sci. USA* 86, 4037–4041 (1989) in studies aimed at defining the specificity domain of *B. thuringiensis* Cry proteins, used recombinant DNA techniques to exchange certain sets of conserved and variable regions between two *B. thuringiensis* Cry protein molecules with markedly different toxicities for larvae of *Bombyx mori*. Exchanging the toxic moiety (conserved regions between amino acids 90 and 332) of the highly toxic protein for the same region from the protein with low toxicity still yielded a protein of high toxicity.

The hypervariable amino acid regions responsible for the host range/specificity of these insecticidal proteins are thought to bind the proteins to specific protein receptors on the microvillar membrane of insect gut epithelia [Hofmann et al., Proc. Natl. Acad. Sci. USA 85, 7844–7848 (1988); Van Rie et al., Science 247, 72–74 (1990)]. Binding the insecticidal protein to the membrane enables the toxic domain of the protein to come in contact with a target protein or form a pore, either of which leads to cell death [Hoefte and Whiteley, Supra]. However, the precise mode-of-action of B. thuringiensis Cry toxins at the molecular level is not yet fully understood.

The insecticidal activity of B. thuringiensis crystal proteins has traditionally been investigated by using crude preparations of spore-crystal mixtures [Burges, H. D. (ed.): "Microbial control of pests and plant diseases 1970–1980" Academic Press, Inc. (London), Ltd., London]. However, the results of these studies are difficult to interpret, especially because many B. thuringiensis strains produce more than one crystal protein simultaneously, therefore, it is difficult to determine the toxicity spectrum and other properties of the individual proteins. Single crystal proteins have so far been obtained by purification from B. thuringiensis [Yamamoto and McLaughlin, Biochem. Biophys. Res. Commun. 103, 414–421 (1982)], or through the introduction and expression of the corresponding genes in heterologous hosts [see references cited in Table 2 of the review article by Hofte and Whitley, Supra].

Attempts have been made to improve the host range of B. thuringiensis strains through the introduction of new crystal protein genes, for example by conjugation of plasmids from other B. thuringiensis strains or through direct transformation of crystal protein genes cloned in a B. thuringiensis replicon [Heierson et al., J. Bacteriol. 169, 1147–1152 (1987)]. Carlton, B. C. [Proceedings of the Conference "Biotechnology, Biological Pesticides and Novel Plant-Pest Resistance for Insect Pest Management" held Jul. 18–20, 1988, organized by Insect Pathology Resource Center, Boyce Thompson Institute for Plant Research at Cornell University, Ithaca, N.Y., USA, pp. 38–43]report the construction of a bifunctional B. thuringiensis strain having activity against Colorado potato beetle and caterpillar insects. The potato beetle activity was generated from a natural isolate of Bt. A strain known to be active against caterpillars was mated with the strain showing potato beetle activity to produce a transconjugant having the desired properties.

Data from in vitro experiments strongly suggest that activated toxins recognize high-affinity binding sites (putative receptors) on the midgut epithelium of susceptible insects only, and that the presence, absence, or modification of these receptors may be an important factor in determining the host range of B. thuringiensis. However, so far this observation has not been utilized in any way in the development of novel bio-insecticides with improved properties and broader host-range. The scarce attempts to improve the host range of B. thuringiensis by using techniques of recombinant DNA technology concentrated on the construction of new B. thuringiensis strains harboring a combination of genes encoding toxins showing activity against different insect hosts.

SUMMARY OF THE INVENTION

We have surprisingly found that the low efficacy of interaction between certain insecticidal toxins, for example B. thuringiensis crystal proteins (Cry proteins, δ-endotoxins), and the gut epithelial cells of certain insects can be efficiently improved by providing an additional protein domain of viral origin to the toxin, which can interact more efficiently with the gut (usually midgut or hindgut) epithelium of the target insect.

It has further been found that a similar increase in the host range or toxicity of insecticidal toxins can be achieved by providing a bacterial protein domain having high affinity to the lipid components of membranes.

This approach that can, for example, be realized by constructing a chimeric protein that not only will improve the toxicity by concentrating more of the toxin on the midgut epithelial cell surface, but also will confer specificity through its receptor binding domain. Accordingly, via construction of chimeric genes of insecticidally active toxins and specific midgut/hindgut binding proteins, chimeric toxin proteins with increased host range and toxicity can be produced.

In one aspect, the present invention relates to a method for increasing the host range or toxicity of an insecticidal protein exerting its activity via interaction with the gut epithelium of insects within its host range, comprising delivering the insecticidal protein to the gut epithelium of a target insect with the aid of an other protein capable of binding to the gut epithelium of the target insect. The other protein may, for example, be of viral origin or, alternatively, may be a bacterial protein or protein domain having high affinity for the lipid components of membranes. If the target insect is within the original host range of the insecticidal protein, the toxicity of the protein can be increased by providing a better binding to the gut of the target insect. On the other hand, this method is suitable for expanding the host range of an insecticidal protein to insects which were not within its original host range.

In another aspect, the present invention relates to DNA comprising a first and a second DNA fragment together encoding a chimeric protein comprising a first protein domain having insecticidal activity exerted via interaction with the gut epithelium of insects within its host range, encoded by the first DNA fragment and a second, viral or bacterial protein domain capable of binding to the gut epithelium of target insects to which the protein domain encoded by the first DNA fragment is not bound or is not efficiently bound, encoded by the second DNA fragment. If the second DNA fragment encodes a bacterial protein domain, that domain is selected of proteins or protein domains having high affinity for the lipid components of membranes.

In a still another aspect, the present invention relates to expression vectors comprising an expression cassette having a DNA sequence as hereinabove defined.

In a further aspect, the present invention concerns chimeric proteins comprising a first protein segment having insecticidal activity exerted via interaction with the gut epithelium of insects within its host range, and a second protein segment capable of binding to the gut epithelium of target insects to which the first protein segment is not bound or is not efficiently bound. The second protein segment is encoded by a second DNA fragment, as hereinabove defined.

In a still further aspect, the present invention relates to a process for the production of such chimeric proteins, which comprises expressing a DNA sequence as hereinabove defined in a recombinant host cell, which is a microorganism or a cell culture transformed with an expression vector containing the desired DNA sequence.

In another aspect, the present invention relates to a recombinant microorganism transformed with an expression vector comprising a DNA sequence as defined above.

BRIEF DESCRIPTION OF THE DRAWINGS

FIG. 10 shows the results of detection of Btt/gp64 fusion protein in *E. coli* by immunoblotting.

FIG. 14 shows the DNA sequence and the deduced amino acid sequence of the gp64 viral membrane glycoprotein of AcNPV.

FIG. 16 illustrates the nucleotide and deduced amino acid sequences of chimeric protein pFAv10.

FIG. 17 shows the nucleotide and deduced amino acid sequences of chimeric protein pFx7.

FIG. 18 shows the nucleotide and deduced amino acid sequences of chimeric protein pFAc13.

FIG. 21 is the nucleotide sequence of PG 14 72kDa+25 kDA.

FIG. 22 is the nucleotide sequence of PG 14 72kDa+27 kDA.

FIG. 23 shows pictures of Heliothis larvae treated with Btt/gp64 fusion proteins in comparison with control.

FIG. 24 shows the results of SDS-PAGE analysis of fusion and non-fusion Btt protein molecules.

DETAILED DESCRIPTION OF THE INVENTION

1. Definitions

The term "gut" as used herein primarily refers to the midgut or hindgut of target insects, since the overwhelming majority of insecticidal proteins exerting their activity via interaction with the gut epithelium interact with these portions of the gut. *B. thuringiensis* crystal proteins are known to bind to the midgut epithelium of insects within their host range.

The term "insecticidal protein" as used in the claims and throughout the specification refers to proteins that cause disease and show toxicity in insects, and exert their insecticidal activity via interaction with the gut cell surface of insects within their host range. In this context, the term "protein" includes naturally occurring and synthetic proteins and protein fragments having insecticidal properties. Naturally occurring insecticidal proteins may, for example, be originated from any protozoan, or metazoan organism, prokaryotic organisms, virioids, rickettsiae, spirochates, prions, etc.

The term "crystal protein" ("Cry" protein) is used to refer to proteins present in the crystalline inclusions produced by sporulating cells of *Bacillus thuringiensis.* These proteins are often referred to in the art as "delta-endotoxins" (δ-endotoxins), and in the present specification the two terms are used interchangeably. Most crystal proteins are believed to be protoxins that are proteolytically converted into smaller toxic polypeptides in the insect midgut. The term "a fragment thereof having insecticidal activity" as used in connection with crystal proteins, relates to any smaller fragment of a crystal protein that shows insecticidal activity, including but not restricted to the smaller toxic polypeptide fragments obtained by proteolytic degradation in the insect midgut. Thus, the latter term specifically includes portions of known crystal proteins of *B. thuringiensis* that have been identified as the "toxic domain" (as opposed to the "binding" portion).

The term "insect" includes insects in different stages of development, i.e. immature and adult insects. Immature target insects are usually in the larval stage of development and are common targets of insecticidal toxins. However, the methods and means provided by the present invention are equally suitable for control of adult insects, such as beetles, cockroaches, locusts, termites, etc. that cause significant economic losses.

The term "expression vector" as used herein, refers to expression vehicles which are capable of expressing DNA sequences contained therein, such sequences being operably linked to other sequences capable of effecting their expression. It is implied, although not always expressly stated, that such expression vectors must be replicable in the host organisms either as episomes or as an integral part of chromosomal DNA. Accordingly, the term "expression vector" has a functional definition, and any DNA sequence which is capable of effecting expression of a specified gene (DNA code) disposed therein, is included within this definition. Expression vectors are often in the form of "plasmids", which are circular double-stranded DNA molecules, which, in their vector form, are not bound to the chromosome. Although plasmids are the most commonly used form of vectors, the invention is intended to include any other forms of expression vectors which serve equivalent functions and which are known in the art or become known in the art subsequently hereto.

In the chimeric protein molecules according to this invention, the first insecticidal protein fragment and the second targeting protein fragment can be located either on the amino terminus or on the carboxyl terminus of the chimeric protein.

"Recombinant microorganisms" are microorganisms which have been transformed with vectors using techniques of recombinant DNA technology.

2. Materials and General Methods

DNA sequences encoding proteins showing insecticidal activity generated via insect-cell surface interaction are known in the art. DNA sequences encoding crystal proteins (43 and 56kD) of *B. thuringiensis* are, for example, disclosed in Hofte and Whiteley, Supra. and in the references cited therein. Proteins (43 and 56kD) from *Bacillus sphaericus* are toxic against mosquitoes. [Bauman, L., et al., *J. Bacteriol.* 170: 2045–2050 (1988); Bauman, P. et al., *J. Bacteriol.* 169: 4061–4067 (1987)]. It will be understood that natural allelic variations of the insecticidally active protein sequences exist and occur from individual to individual. These variations may be demonstrated by one or more amino acid differences in the overall sequence, or by deletions, substitutions, insertions, inversions or additions of one or more amino acids in the amino acid sequence. DNA sequences encoding such variants of naturally occurring insecticidally active proteins are within the scope of the present invention. The DNA sequences encoding the insecticidally active proteins used in accordance with the present invention may be isolated from their natural sources, excised from vectors (plasmids) that are commercially available or are in wide circulation among scientists, or, alternatively, may be synthesized by methods known in the art.

Figure 1:
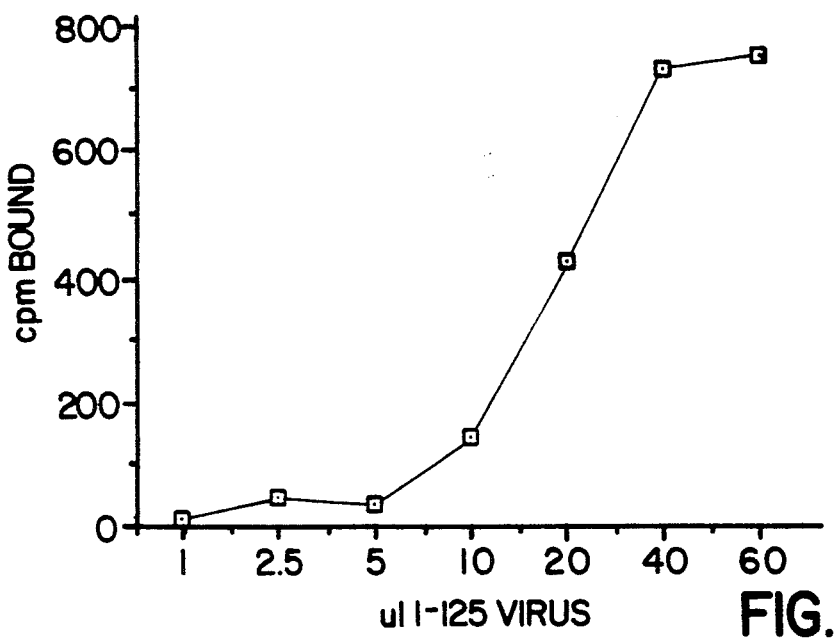
FIG. 1 illustrates the saturation kinetics of $^{125}$I-labeled (Autographa californica Multiple Nuclear Polyhedrosis Virus (AcMNP) virus binding to brush border membrane vesicles (BBMV) selectively isolated from the intestinal tissue of the larvae of *Trichoplusia ni*. Different amounts of I-125 labeled free virus (1–60μl) in PBS+Ca+Mg buffer were added to the membrane vesicles (1–2 βl/5–10 μmg protein) in a total volume of 100–400 μl and incubations were carried out at 20° C. for 60 min. before the vesicles were pelleted and washed. Control tubes containing the indicated volume of I-125 labeled virus (1–60μl) but no membrane vesicles, were incubated, pelleted and washed as with the tubes containing membrane vesicles and counted using a scintillation counter. These background counts were deducted from the membrane vesicle bound counts before they were plotted. A similar pattern of binding kinetics was observed when the binding was done with higher amounts (2–3μl) of membrane vesicles. The actual counts bound to the BBMV varied according to the efficiency of virus labelling (specific activity). Initial experiments indicated that at least 30 min. incubation with labeled virus is required for maximum binding.
Figure 2:
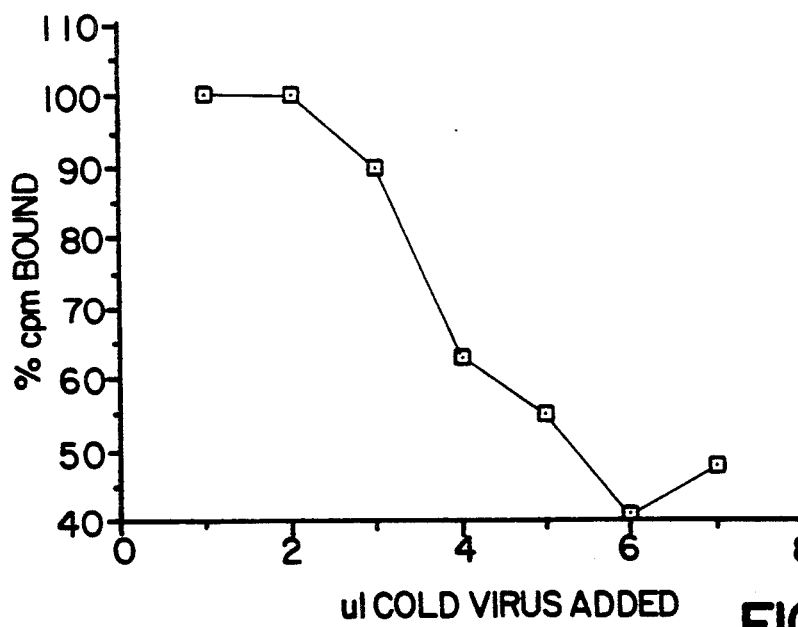
FIG. 2 illustrates the inhibition of $^{125}$I-labeled AcMNP virus binding to brush border membrane vesicles (BBMV) in the presence of unlabeled cold virus particles in the reaction mixture. Binding of the I-125 labeled virus to the membrane vesicles were carried exactly as described before for FIG. 1 except that appropriate amount (1–10μl) of unlabeled free virus was added to the membrane vesicles in cold (4° C.) immediately before the labeled virus was added, mixed well and the incubation at 20° C. was started. The free unlabeled virus was obtained by homogenizing the viral preparation in a 1ml homogenizer several times (15–20x), spinning the homogenate at 15K rpm for 10 minutes in the microfuge and using only the supernatant. The above figure is a typical binding reaction performed in the presence of a certain concentration of unlabeled virus. The actual pattern varied depending upon the concentration of the unlabeled free virus particles present in the incubation mixture.
Figure 3:
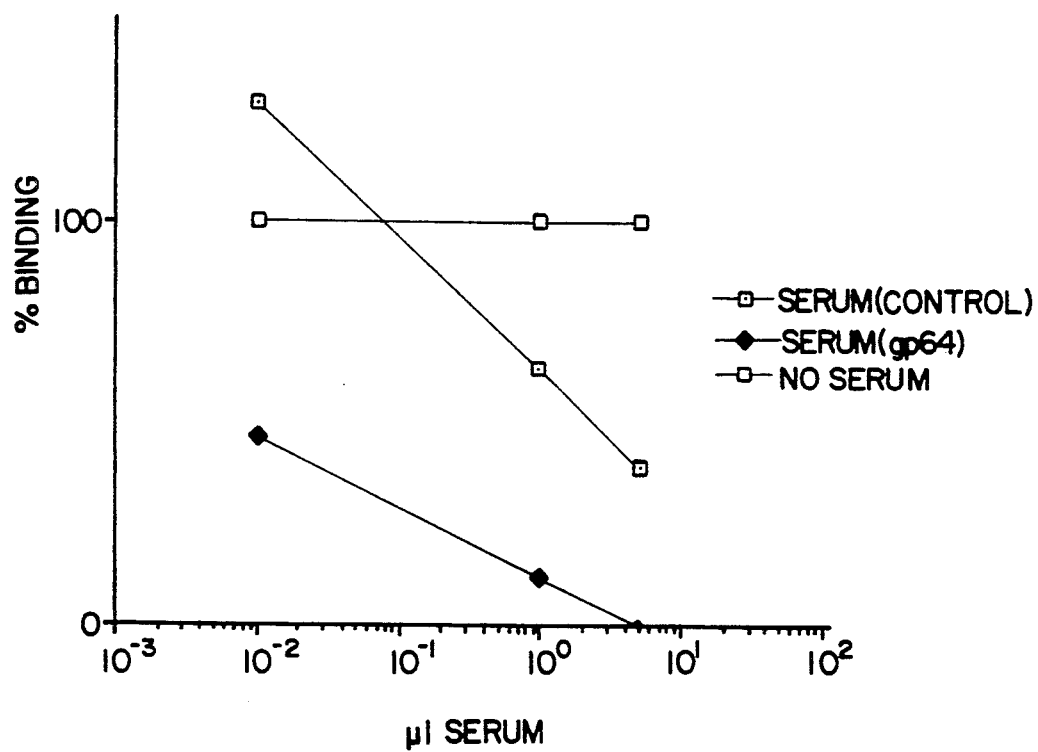
FIG. 3 illustrates the specificity of the inhibition of the binding of the AcMNP virus to the brush border membrane vesicles (BBMV) by the polyclonal antibody to viral gp64 containing rabbit serum and preimmune serum. I-125 labeled AcMNP virus binding in the presence or absence of serum were carried out exactly as described before. Dilution of the serum was done in PBS+Ca+Mg buffer (1:100 and 1:500) just before the virus was added to the serum and preincubation on ice for 15 min. was started. After preincubation of virus and serum (in a total volume of 15–20μl) on ice, the mixture was added to the membrane vesicles, mixed well and incubation at 20° C. for 60 min. was started. Washing of the membrane vesicle pellets was carried out as described before.
Figure 4:
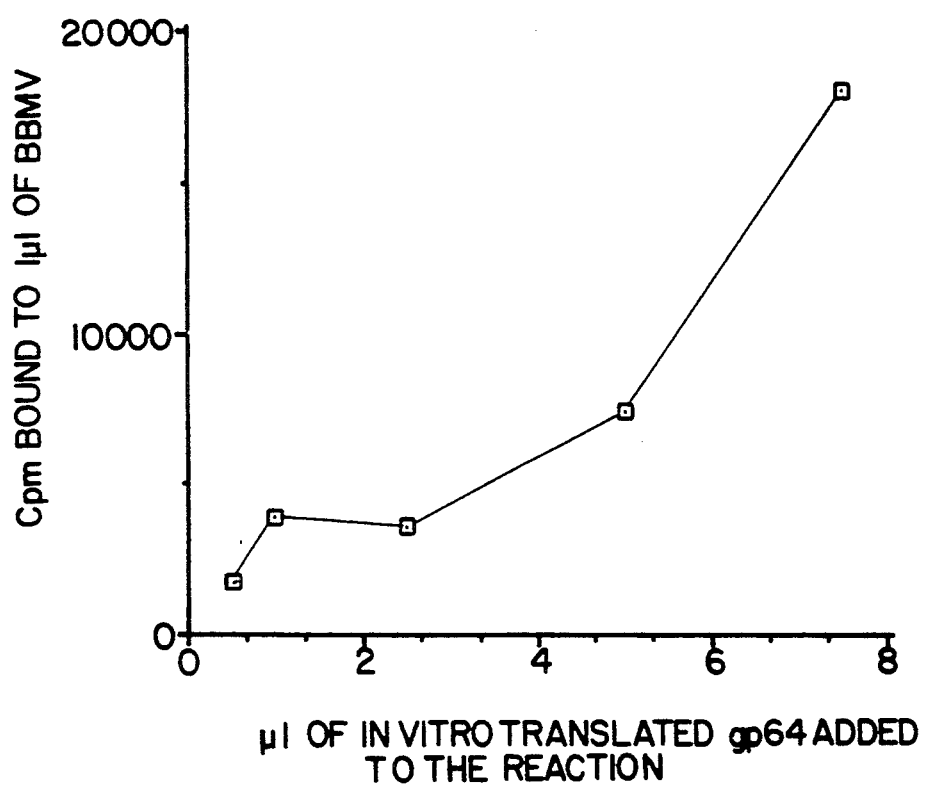
FIG. 4 illustrates the binding of AcMNP viral gp64 protein (non-glycosylated) to BBMVs of *Trichoplusia ni*. S-35 methionine and H-3 Leucine labeled ACMNP viral envelope protein gp64 (non-glycosylated) was made in vitro by translating the in vitro made mRNA (using SP6 RNApolymerase, Promega) for gp64 protein using the rabbit reticulocyte cell extract (Promega) for two hours at 37° C. The labeled gp64 was separated from the unincorporated S-35 methionine and H-3 Leucine by filtering the extract using a 1.5ml filtration unit (Millipore) with a cut-off range of 10K dalton and washing the filtrate with PBS buffer 3x each 1.5ml. Filtrations and washings were done at 4° C. in a Sorval refrigerated centrifuge. This filtrate was used for all the binding experiments. Binding to BBMV was carried out exactly as before except that incubations were carried out for only 15 min. In a typical experiment, 1–10μl of the above filtrate was used for binding. Control tubes carried equal volumes of labeled gp64 protein but no BBMV. These background counts were deducted from the test-samples and then plotted. 1μl filtrate contained about 100,000 cpm.
Figure 5:
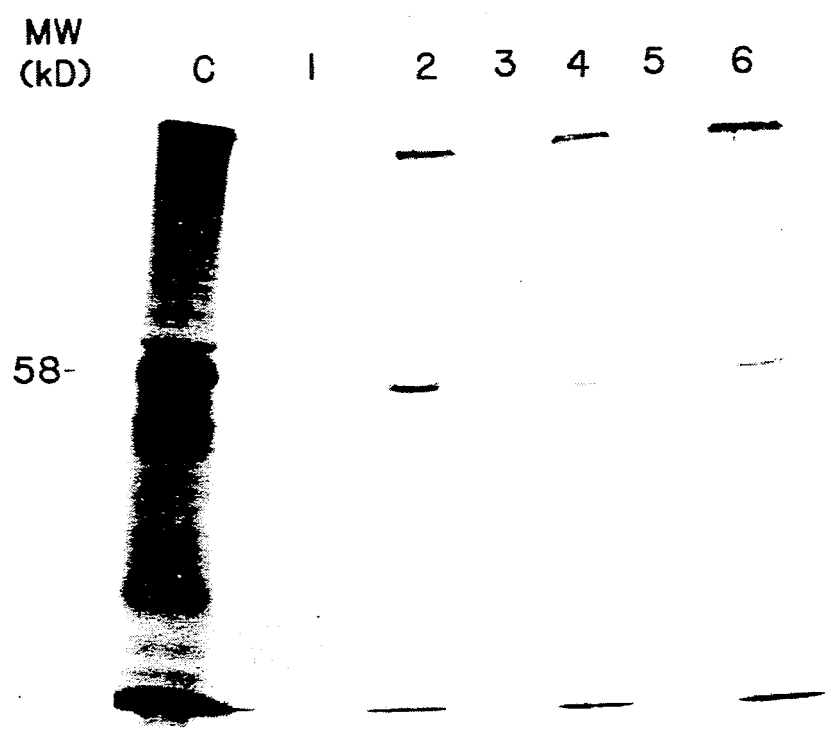
FIG. 5 shows the SDS-gel profile of $^{35}$S methionine labeled gp64 (non-glycosylated) that is bound to BBMVs of Trichoplusia ni. S-35 met and H-3 leucine labeled gp64 protein was incubated with the BBMV as before except for the conditions described for each lane. C. Input gp64 material 1.,3 and 5: Background bound material bound to tubes (in the absence of BBMV) with 1ul gp64 filtrate added. Lanes 2, 4 and 6: labeled material bound to 1μl (2, 4) and 2μl (6) BBMV. All binding reactions were carried out for only 15 min. All BBMV pellets were washed as before and loaded onto gel.
Figure 6:
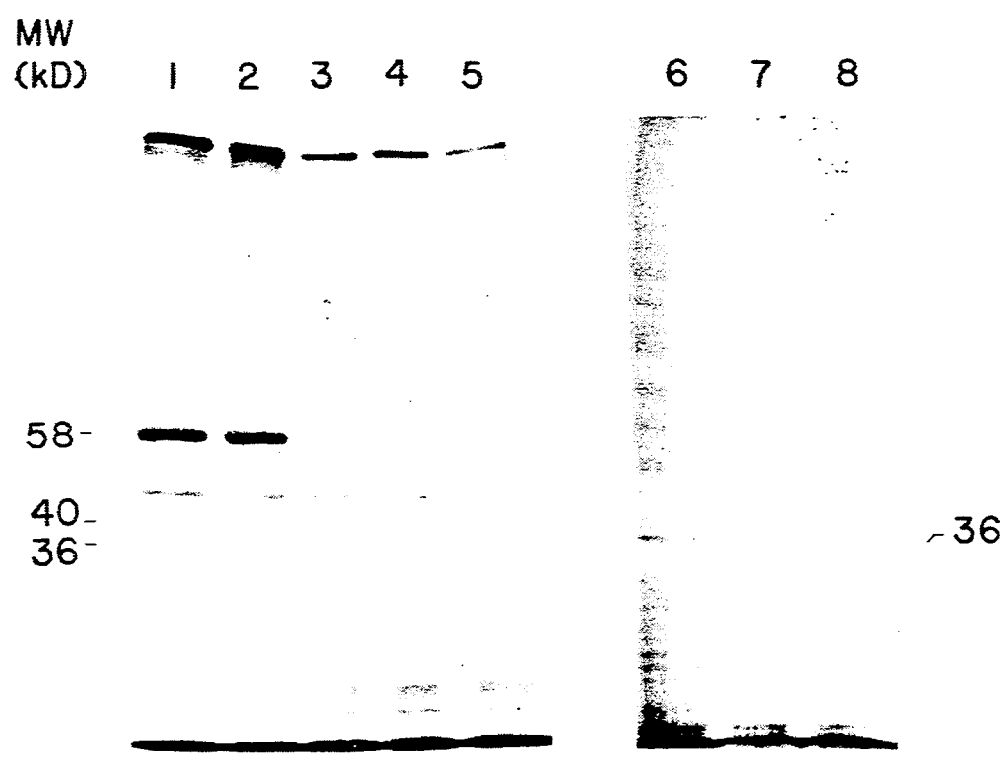
FIG. 6 shows the results of processing the gp64 protein (non-glycosylated) bound to BBMVs isolated from Trichoplusia ni intestinal tissues. Binding of the S-35 met and H-3 Leu labeled gp64 protein (non-glycosylated) to the BBMV was carried out exactly as before except for the changes that are mentioned for each sample. Samples were resuspended in 2x SDS-gel buffer and loaded onto 10% polyacrylamide gels. The gel was fixed, impregnated with 1.6% sodium salicylate, dried and exposed to Kodak x-ray films. Lane (1). In vitro made gp64 protein (after filtration with the 10K dalton filter). (2). In vitro made gp64 protein incubated at 20° C. in the presence of 2μl BBMV incubated for (3) 30 min., (4) 60 min. and (5) 90 min. Samples c-e were loaded onto gel after incubation at 20° C. without washing the BBMV. Lane f-h contain labeled gp64 protein samples incubated with different amounts of BBMV, namely (6) 10μl, (7) 15μl and (8) 20μl BBMV for 60 min., washed with PBS+Ca+Mg+BSA-buffer 3x and the BBMV pellet loaded onto the gel. The arrows indicate the intact and processed gp64 protein.
Figure 7:
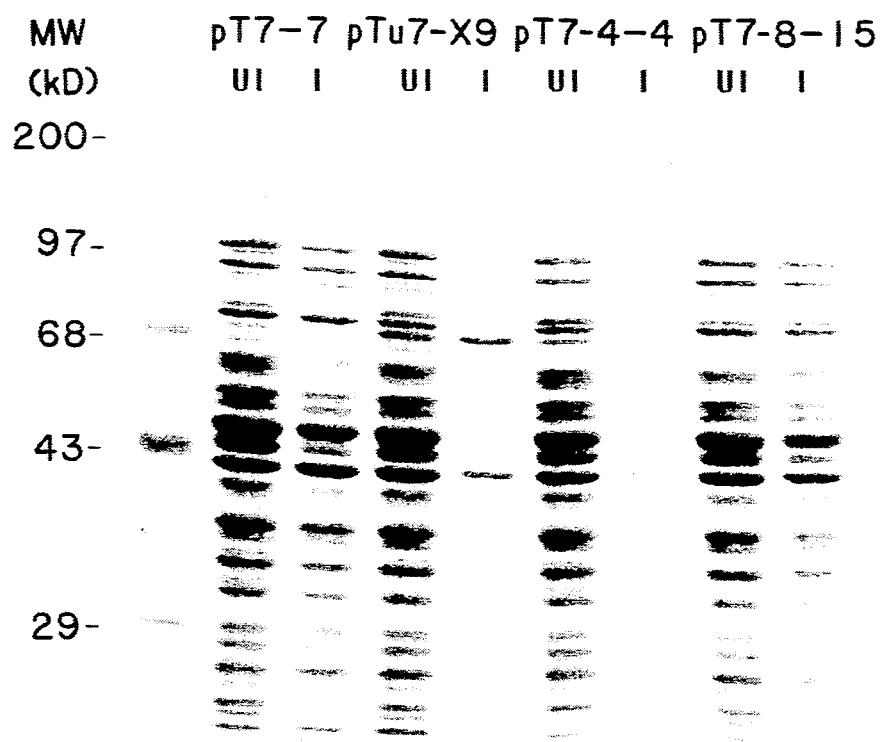
FIG. 7 shows the SDS-gel profile obtained following expression of Coleopteran toxin in *E. coli*.
Figure 8:
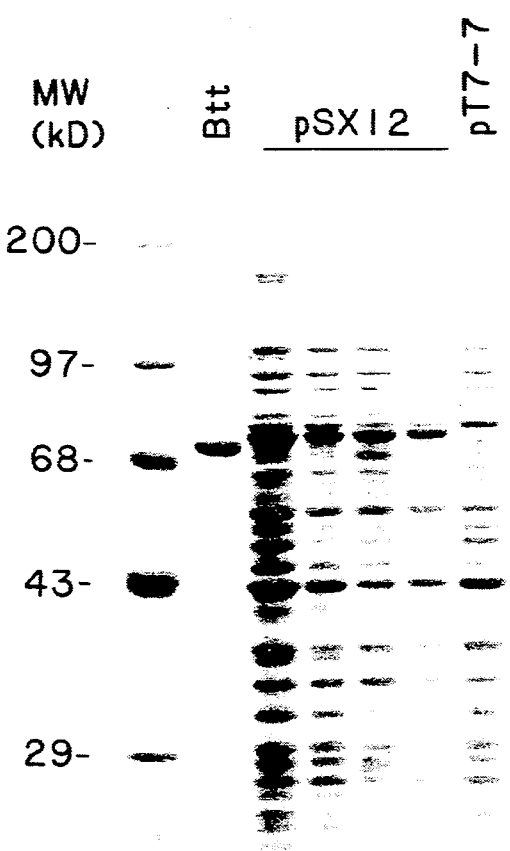
FIG. 8 shows the SDS-gel profile obtained following expression of modified Coleopteran toxin in *E. coli*.
Figure 9:
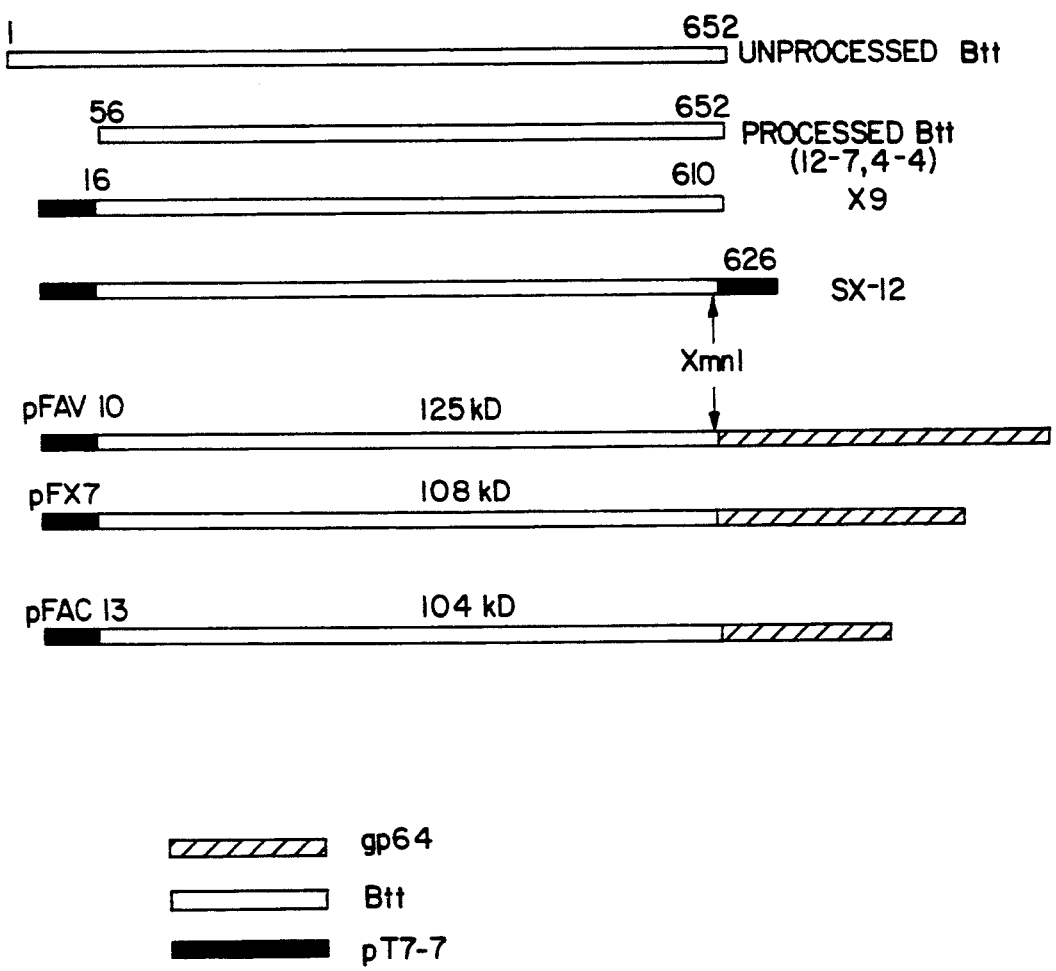
FIG. 9 illustrates the Btt/gp64 gene fusions constructed in accordance with the invention.
Figure 11:
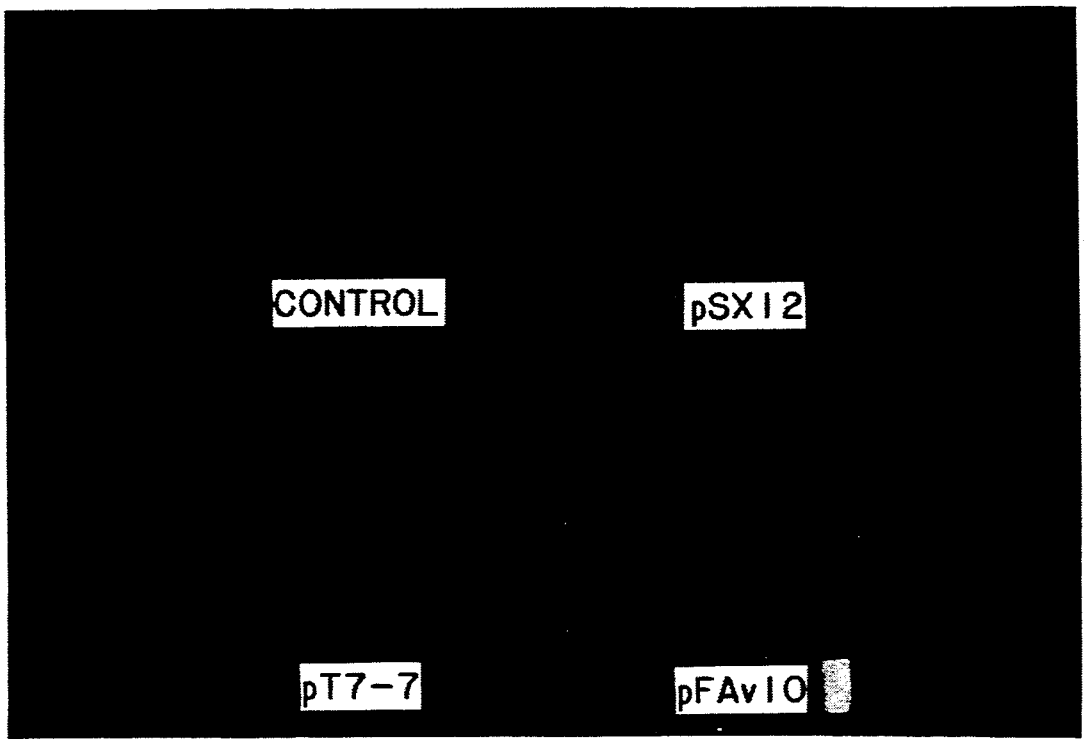
FIG. 11 shows pictures of surviving *Trichoplusia ni* neonate larvae treated with Btt/gp64 fusion proteins in comparison with control.

A viral membrane (surface) glycoprotein of the extracellular form of AcNPV (Autographa californica Nuclear Polyhedrosis Virus), gp64, has been isolated and sequenced in this laboratory. The DNA sequence and deduced amino acid sequence of gp64 were first presented at the 1988 Annual Meeting of the American Society for Virology in the University of Texas at Austin—Jun. 12-16, 1988, and are shown in FIG. 14 herein.

Although the present invention is illustrated by the use of this specific protein, surface proteins of all insect viruses which enter through the gut are suitable for practicing the invention.

A protein that has been found to show high affinity to a large variety of membranes is the Cyt A protein of *Bacillus thuringiensis subsp. israelensis* (BTI) and of the PG-14 strain of *B. thuringiensis subsp. morrisoni* (BTM). This is a protein of 27.3-kDA which shows no significant amino acid homology with any of the Cry proteins of *B. thuringiensis*. More importantly, it has very different biological properties, having a broad host range, including mosquitoes and other nematocerous flies in vivo, and an extraordinary broad host range against cells in vitro, including those from a wide variety of invertebrates and vertebrates [Thomas and Ellar, *FEBS Microbiol. Lett.* 154, 362-368 (1983); and *J. Cell Sci.* 60, 181-197 (1983); Chilcott, C. N. and D. J. Ellar. *Journal of General Microbiology* 134, 2551-2558 (1988); Federici et al. The parasporal body of BTI; Structure, protein composition, and toxicity. In "Bacterial Control of Mosquitoes and Blackflies: Biochemistry, Genetics, and Applications of *Bacillus thuringiensis* and *Bacillus sphaericus*" (H. De Barjac and D. Sutherland, editors), Rutgers University Press, New Brunswick, N.J., 1990.]. The nucleotide sequence of the 27.3-kDA cytolytic protein is, for example, disclosed by Galjart et al., *Curr. Microbiol.* 16, 171-174 (1987), and, for BTI, by Waalwijk, C., et al., *Nucleic Acids Res.* 13, 8206-8217 (1985).

Although the Examples illustrate the expression of certain specific DNA sequences according to the present invention in *E. coli*, using specific expression systems, it will be understood that the expression may be performed in cells of a wide range of prokaryotic (including *B. thuringiensis*) and eukaryotic organisms including plants (transgenic), using a wide range of vectors for transformation. In general, prokaryotes are preferred for cloning and expression of DNA sequences according to the present invention. Particularly preferred are cells of bacteria, preferably *E. coli*. Other suitable prokaryotes include bacilli, such as *Bacillus subtilis*, various Pseudomonas species, etc.

Eukaryotic microorganisms, such as yeasts, may also be used for practicing the present invention. *Saccharomyces cerevisiae* (S. cerevisiae, baker's yeast) is the most commonly used, however, numerous other yeasts are also well known in the art and routinely used for the expression of foreign proteins. Such yeast include, for example, the methylotrophic yeast *Pichia pastoris* (*P. pastoris*), Aspergillus nidulans, etc.

Plasmids suitable for transformation of *E. coli* are well known in the art and are illustrated in the Examples hereinafter. Such plasmids must contain promoters which can be used by the microorganism for expression of its own proteins. One of this promoters is the lac promoter, the use of which is illustrated in the Examples. Another promoter system widely used for the expression of foreign proteins in *E. coli* is the tryptophan (trp) promoter/operator system [Goeddel et al., *Nucleic Acids Res.* 8, 4057 (1980)]. While these are most commonly used, other microbial promoters are also known and used in the art, and are suitable for practicing the present invention. The expression plasmids ordinarily carry markers providing for phenotypic selection in the transformed cells. In *E. coli*, typically antibiotic resistance sequences, for example genes for ampicillin and tetracycline resistance, are used for selection. Probably the most commonly used *E. coli* expression vectors are the plasmid pBR322 [Bolivar et al., *Gene* 2, 95 (1977)]and its derivatives.

Suitable promoters for yeast vectors include the promoters for 3-phosphoglycerate kinase [Hitzeman et al., *J. Biol. Chem.* 255, 12073 (1980)], acid phosphatase, and GPD portable promoter [Bitter, G.A., *Methods in Enzymology*, 152, 673-684 (1987)]. In general, any plasmid vector containing yeast-compatible promoter, origin of replication and termination sequences is suitable for expressing DNA sequences of the present invention, to produce the desired chimeric proteins.

Additionally, chimeric toxin proteins with new insecticidal properties and/or increased toxicity generated by this approach can be expressed in commercially important plants thus making them resistant to variety of insect pests instead of few. Utilizing the Ti plasmids which carry CaMV35S promoter, these chimeric proteins can be expressed in plants like tomato, tobacco, cotton, potato etc., [Vaeck, M. et al., *Nature*, 327, 6125, 33-37 (1987); Fischnoff, D. A. et al., *Biotechnology*, 5, 807-813, (1987)].

Expression of heterologous proteins in prokaryote or eukaryote microorganisms is well known in the art. The construction of suitable expression vectors (plasmids), and the operable ligation of the DNA sequences of the present invention with such plasmid vectors are well within the knowledge of a skilled artisan.

Cultures of cells derived from multicellular organisms, vertebrates or invertebrates, may also be used as hosts, cultures of vertebrate cells being preferred. Examples of suitable vertebrate cell lines are Chinese hamster ovary (CHO) cell lines, HeLa, COS-7, AGMK, Rat-1 cell lines. Expression vectors for such cells ordinarily include an origin of replication, a promoter located 5' of the gene to be expressed, transcription terminator sequences, as well as any necessary ribosome binding sites, polyadenylation sites, etc.

The fragments of the expression cassettes of the present invention are in operational association, i.e. the DNA sequences encoding the desired chimeric proteins are positioned and oriented functionally with respect to the other fragments of the expression cassette, such as the promoter, and transcription terminator sequences. The chimeric proteins may be expressed as fusion proteins, containing protein sequences homologous to the host organism used for expression, or as non-fusion protein products. Fusion proteins that can be processed to provide the desired chimeric protein in active form are within the scope of the present invention.

Methods for transforming host organisms are well known in the art, and are, for example, disclosed by Maniatis et al., in Molecular Cloning: A Laboratory Manual, Cold Spring Harbor Laboratory Press, Cold Spring Harbor, N.Y., USA (1982).

The chimeric proteins of the present invention can be delivered to insects in a variety of ways including as insecticidal protein baits, as recombinant microbial insecticides, and through transgenic plants. Insecticidal compositions using the chimeric proteins of the present invention may be prepared in a known manner, using carriers and other additives well known in the art.

3. Description of Preferred Embodiments

According to a preferred embodiment of the invention, DNA sequences encoding *B. thuringiensis* δ-endotoxins and the gp64 viral membrane glycoprotein of AcNPV are operably linked, and the combined DNA sequence is expressed in host organisms to produce chimeric Bt/gp64 chimeric toxin proteins.

AcNPV can infect 11 different tissues (fat body, tracheal matrix, hypodermis, Malpighian tubules, muscle, hemocytes, ganglia, midgut, hindgut, juvenile tissue and testes) in 33 species of lepidopteran larvae (19 species of family Noctuidae). The viral gene product, gp64 is a component ('peplomers' or 'spikes') of the extracellular form of AcNPV. Evidence in the literature indicates that this protein interacts with cell surface receptor(s) of various host (lepidopteran larva) tissues facilitating viral entry into the cell. It is known that the extracellular virus is utilizing a common unbiquitous receptor in various insect larval tissues. While evaluating the infectivity of extracellular form of AcMNPV in comparison with the occluded form of AcMNPV, researchers have indirectly shown that, through feeding (per os) the extracellular form of AcMNPV can infect the larval host caterpillars at very low levels (Volkman, L. E., and M. D. Summers, *J. Invertebr. Pathol.*, 30: 102–103 (1977); Keddie, B. A., and Volkman, L. E., *J. Gen. Virol.*, 66, 1195–1200 (1985).) These results indirectly indicate that at least some extracellular AcMNPV particles might have entered through midgut epithelial cells possibly through receptor mediated endocytosis (inventor,s interpretation of the above data) using gp64. Although no role has been assigned to the gp64 to interact with the midgut receptors in the natural life cycle of the virus, because of the broad tissue tropism and host range of this virus (Vail, P. V. et al., *J. Invertebr. Pathol.*, 21, 198–204 (1973); & IVth Int. Colloq. Insect Pathol. 1971) it is conceivable that the receptors for the gp64 is also present in the midgut epithelial cell surface, thus facilitating the entry of extracellular AcMNPV. The present inventors have experimentally found that midgut epithelial cells also possess the common ubiquitous receptor for AcNPV gp64. Because of the AcNPV's broad host range and tissue tropism, gp64 has considerable potential to improve the host range and toxicity of currently available microbial insecticides. The AcNPV gp64 receptor binding domain interacts with its specific host midgut receptors, whereby more chimeric toxin is concentrated on the midgut epithelial cell surface, and toxicity is improved. Even more importantly, by providing an additional receptor binding domain to the Bt δ-endotoxin, specificity is improved, and the host range of Bt toxins can be extended to insects to which they are not or not sufficiently toxic. In other words, gp64 gene sequences can be used as midgut targeting signals for bacterial endotoxins, including Bt endotoxin.

According to another preferred embodiment of the invention, a *B. thuringiensis* toxin is combined with a 27.3-kDA protein of *B. thuringiensis* (from subspecies israelensis - Bti, and morrisoni - Btm) which is known to have high affinity for the lipid portion of cell membranes. This protein was shown to be highly hydrophobic [Galjart et al., Supra: and Ward and Ellar, *J. Mol. Biol.* 191, 1–11 (1986)], and binds to cell membranes readily at low concentrations, forming aggregates at higher concentrations that disrupt membranes through a detergent-like mode of action [Chow et al., *Appl. Environm. Microbiol.* 55, 2779–2788 (1989)]. The broad species host range of this protein is due to its high hydrophobicity and affinity for unsaturated fatty acids, constituting a principal component of the lipid bilayers of cell membranes [Thomas and Ellar, *J. Cell Sci.* 60, 181–197 (1983); and Ward et al., *J. Mol. Biol.* 191, 13–22 (1986)]. As a result of these properties, unlike any other Bt protein, this protein in vitro readily disrupts cells such as mouse fibroblasts, rat, horse, sheep and human erythrocytes, and insect cells such as those from numerous species of mosquitoes, other flies, and lepidopterans [Thomas and Ellar, *FEBS Microbiol. Lett.* 154, 362–368 (1983); Davidson and Yamamoto, *Current Microbiol.* 11, 171–174 (1984); and Chilcott and Ellar, Supra]. Moreover, the protein expressed from the cloned gene encoding this protein has been shown to be toxic to mosquito larvae in vivo, with an $LD_{50}$ of 125 ng/ml [Ward et al., *J. Mol. Biol.* 191, 13–22 (1986)]. Other indications of the broad host range of this protein are found in its activity against nematodes [Bone et al., *J. Parasitol.* 73, 295–299 (1987)].

After ingestion by insects, the Cyt A protein is cleaved by midgut proteases under alkaline conditions to a relatively resistant core of 25-kDA [Armstrong et al., *J. Bacteriol.* 161, 39–46 (1985); Ibarra and Federici, *J. Bacteriol.* 165, 527–533 (1986); and Gill et al., Supra]. This core has all the biological properties of the 27.3-kDA protein from which it is cleaved. It causes no toxicity to vertebrates when ingested, however, because it is apparently rapidly degraded under the highly acidic conditions present in vertebrate stomachs [Thomas and Ellar, *FEBS Microbiol.*, Supra].

The Cyt A protein of the above isolates are genetically very similar, differing only in the base at position 310 (cytosine in the BTI gene, guanine in the BTM gene; which results in proline at amino acid position 82 in BTI and alanine in BTM; Galjart et al., Supra).

The binding of the 27.3-kDA protein is apparently dependent on the presence of unsaturated fatty acids in the lipid fraction of the cell membrane. Current knowledge indicates that binding is not dependent upon the presence of specific protein receptors in the target membrane.

It is a widely known general property of all biological cell membranes that they are composed of a fluid lipid bilayer which contains a diversity of proteins with different functions. The microvilli of the insect gut epithelia cells have these same properties [Chapman, The Insects-Structure and Function, Elsevier, N.Y. 1971, pp. 819].

Figure 20A:
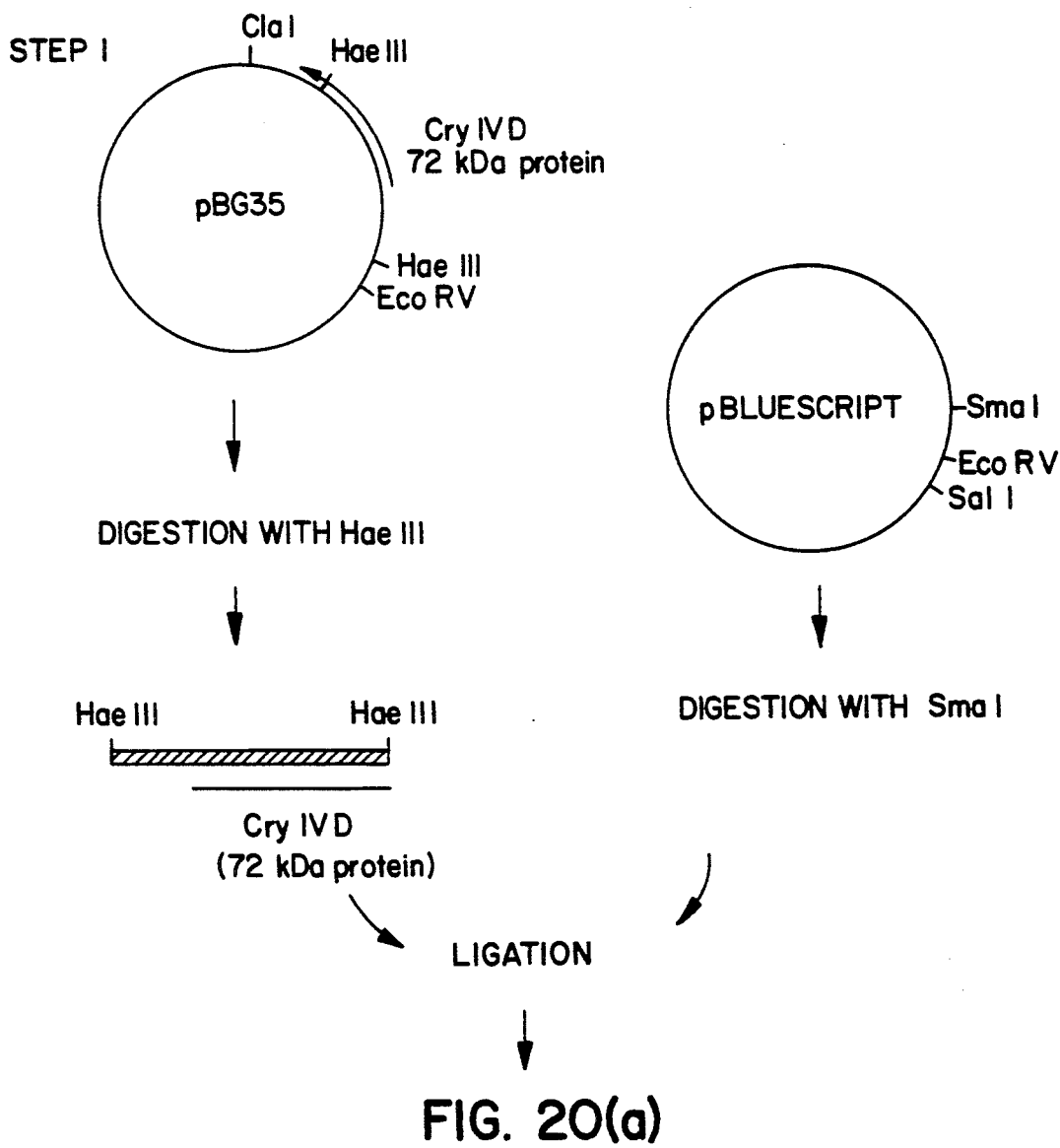
FIGS. 20*a*, 20*b* and 20*c* illustrate the construction of a chimeric Bt Cry-Cyt A gene.
Figure 20B:
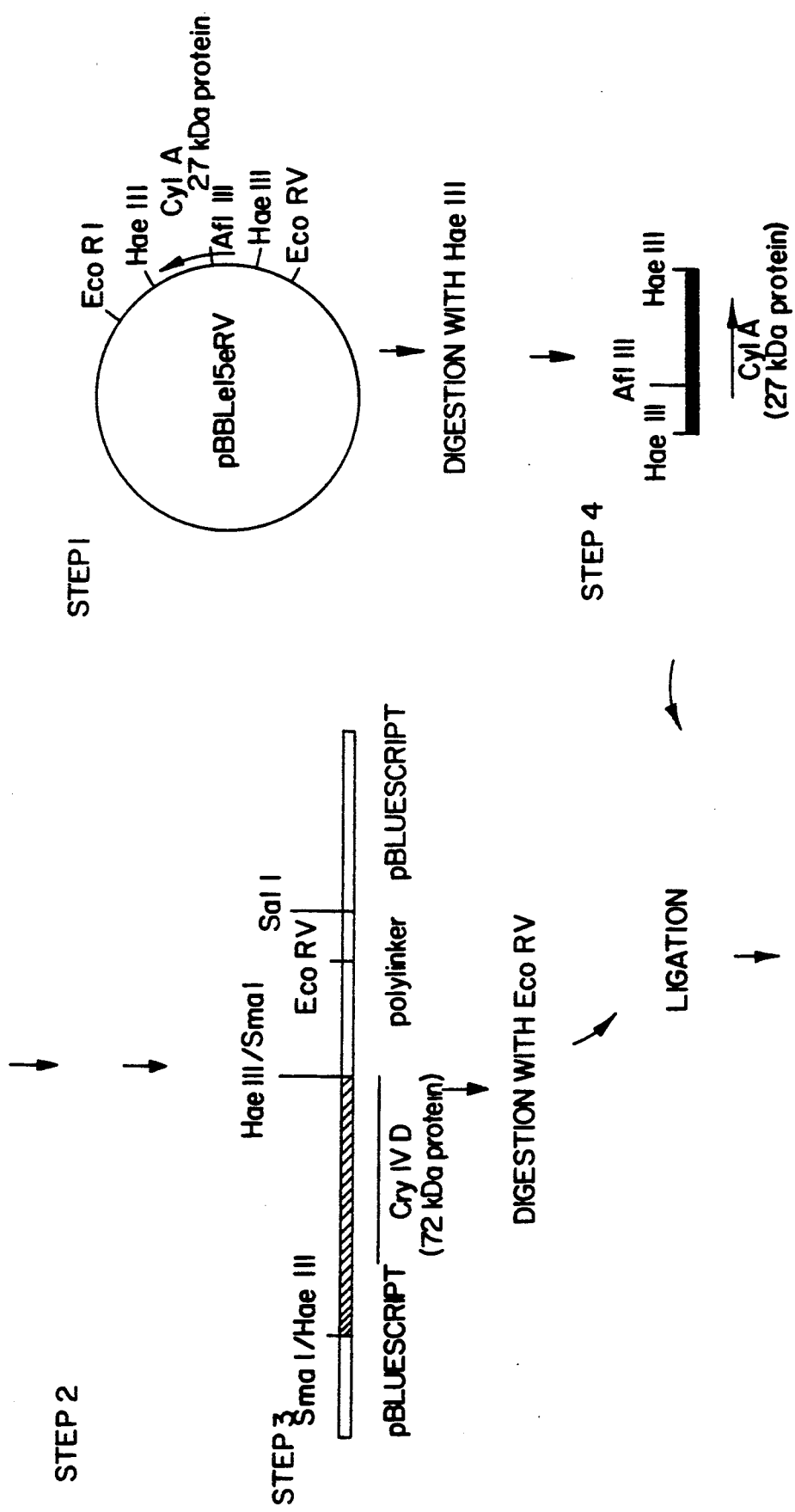
Figure 20C:
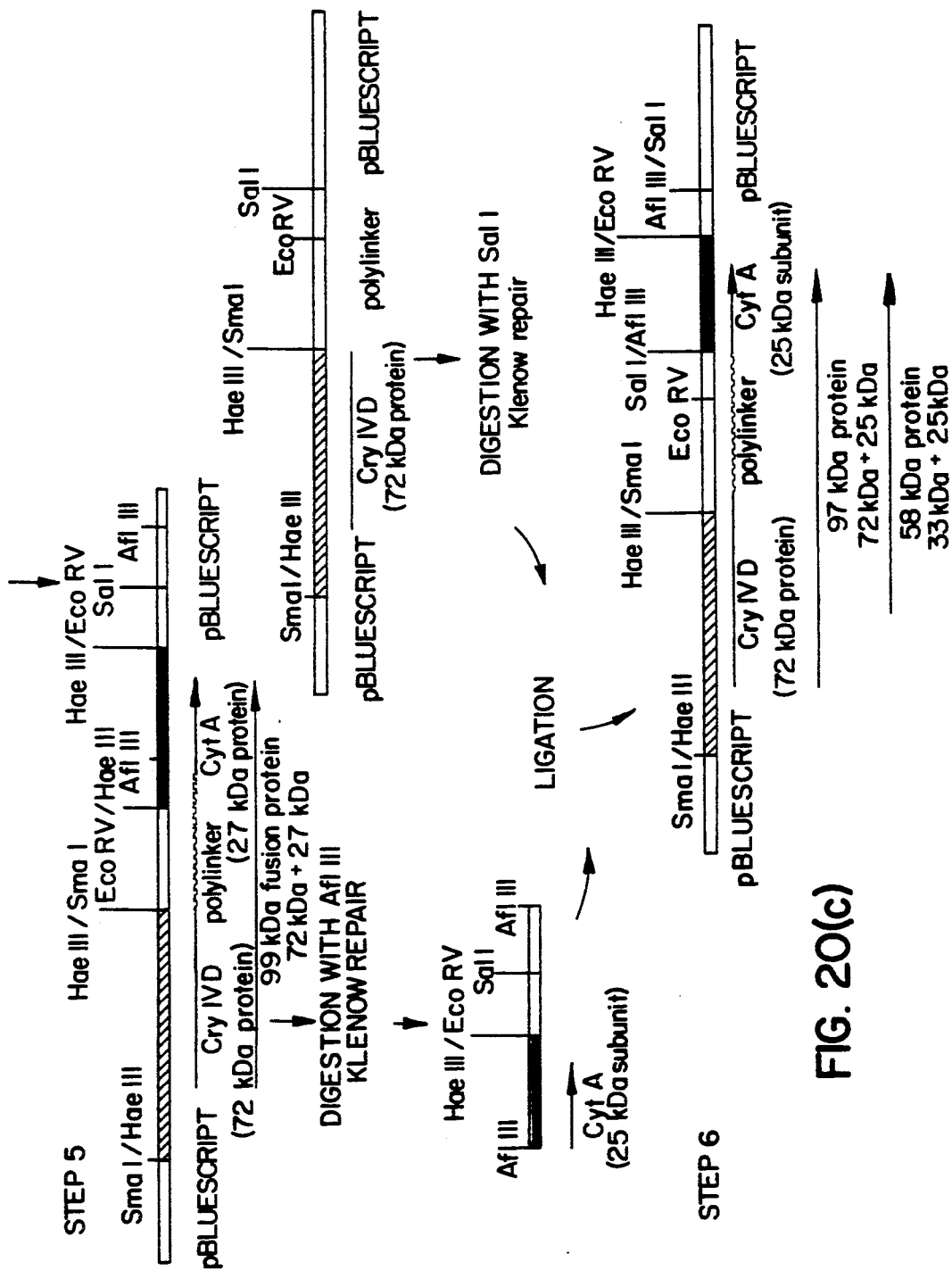

The procedure for the construction of a chimeric BT Cry-Cyt A gene can be outlined as follows (see FIGS. 20a–c):

Step 1. The genes encoding the protein domains to be fused are cloned and prepared for fusion.

The Cyt A gene (encoding the 27.3-kDa cytolytic protein) and the Cry gene (encoding a 65-72-kDa insecticidal protein) are cloned from appropriate bacterial species. In the case illustrated in Example 2, both genes were cloned from the PG-14 strain of *Bacillus thuringiensis subso. morrisoni*. Subsequently, the gene Cyt A was excised from the clone pMI by digestion with EcoRI. This EcoRI fragment carrying the whole Cyt A gene was cloned into the EcoRI site of the vector pBUESCRIPT in both orientations to yield the clones PBBe14e and PBBe15e. Digestion of the clone pBBe15e with EcoRV followed by ligation yielded the clone pBBe15eRV. This procedure deleted nonessential regions of the original clone. The gene Cry IV D was subcloned from pMl by double digestion with ClaI-EcoRV. This fragment was inserted in pBR322 in the ClaI/EcoRV sites to yield the clone pBG35.

Step 2. The gene carrying the start codon is truncated in its 3'-end an subcloned in the polylinker of a vector to allow in-frame cloning with the second gene.

In the specific case described in Example 2, a 3.5kbp HaeIII fragment. The only HaeIII site present in the Cry IV D gene is located 32 base pairs upstream from the stop codon. This digestion yields the Cry IV D gene except for the last 32 nucleotides, which include the stop codon. This fragment was cloned into the SmaI site of pBUESCRIPT KS (in an orientation suitable for in vitro transcription-translation using T7 RNA polymerase) to yield the clone pBBh13s.

Step 3. The junction between the 3' end of the inserted gene and the 5, end of the cloning site in the polylinker is sequenced to ensure in-frame cloning.

In this the junction between the 3' end of Cry IV D and the 5' end of the SmaI site in the polylinker of pBUESCRIPT KS was sequenced with Sequenase using the M13-pUC reverse primer to ensure both the proper orientation and in-frame cloning.

Step 4. Preparation of the gene fragment encoding the relevant domain of the Cyt A protein with sites appropriate for in-frame cloning.

The clone pBBe15eRV was digested by HaeIII and used as a source for a 2 kbp fragment carrying the entire coding sequence of the Cyt A gene. There is no HaeIII site within the coding sequence of the Cyt A gene. This enzyme cuts 35 nucleotides upstream from the start codon, and the sequence between the HaeIII site and the start codon does not contain a stop codon.

Step 5. The coding sequence of the second is inserted downstream, in-frame with that of the first gene.

In the present case, the 2 dbp HaeIII fragment containing the whole coding sequence of the Cyt A gene was inserted in the EcoRV site of the plasmid pBBh13s. This site is located downstream from the SmaI site used for insertion of the HaeIII fragment carrying the truncated Cry IV D gene. The ligation has been performed and the recombinant bacteria are being screened to ensure the two genes are fused in the proper orientation. That the cloning is in-frame will be confirmed by in vitro transcription and translation.

Step 6. The gene encoding the second protein is truncated to yield a sequence encoding the binding fragment, and then cloned in-frame with the first gene.

In this case, the Cyt A gene present in the plasmid resulting from Step 5 is cut with the enzyme AflIII. This enzyme recognizes two sites in this plasmid, one in the coding sequence of Cyt A and the other in pBUESCRIPT 419 base pairs downstream from the SalI site where Cyt A is inserted. The Afl III site in the coding sequence of Cyt A is located at the exact beginning of the sequence for the 25-kDa protein. The cloning of this fragment in frame with the Cry IV D gene will be performed by inserting the AflIII fragment described above (after repair with Klenow) into the SalI site of the polylinker (also repaired with Klenow).

The resulting fusion protein will have a size of 97-kDa (72-kDa +25-kDa) and will generate a subunit of 58-kDa (33-kDa +25-kDa) in the insect midgut.

Although the invention is illustrated by construction of chimeric proteins, utilizing the approach provided by the present invention, other methods can also be designed for increasing the host-range of Bt toxins. For example, a baculovirus (nuclear polyhedrosis virus of any insect virus) which has both midgut binding protein and an insecticidal protein on its surface could be used as a delivery vehicle for insect toxin proteins. Alternatively, even a baculovirus infected insect cell which has both midgut binding protein and an insecticidal protein on its surface, could be used as delivery vehicle for insect toxins. This can, for example, be designed by expressing the insecticidal toxin protein as an integral transmembrane protein using a baculovirus vector. This process generates an infected insect cell containing both the binding domain (e.g. gp64) and insecticidal proteins on its surface. If such infected cells (freeze dried or lyophilized) are fed to caterpillars, gp64 would bind strongly to midgut epithelial cells thus bringing the neighboring insecticidal toxin protein to reach or interact with its target. Thus surface proteins of viruses could be used as delivery vehicles or specificity determinants for variety of insecticidal proteins which do not possess broad specificity. All these methods are within the scope of the present invention.

Further preferred embodiments of the present invention are illustrated by the following non-limiting Examples.

4. Examples

Example 1

A. Methods a. Isolation of Membrane Vesicles from Intestinal Tissues

Membrane vesicles were isolated from the intestinal tissue of the larvae of *Trichoplusia ni* (H bner) *Comp. Biochem. Physiol.* 86A, 301–308 (1987) as described by Wolfersberger, M. et al. Healthy larvae of the 3–4 th instar were chilled in petri dishes over ice and the external skin was cut open with micro dissection scissors and the midgut was gently pulled out with minimum association of the surrounding tissues. The long midgut was vertically cut open and the internal diet was rinsed free from tissues in ice cold buffer A (17 mM Tris-HCl, pH7.5 with 300 mM mannitol and 5 mM EGTA) and placed in cold before blotted, weighed and stored frozen at $-80°$ C.

Figure 12:
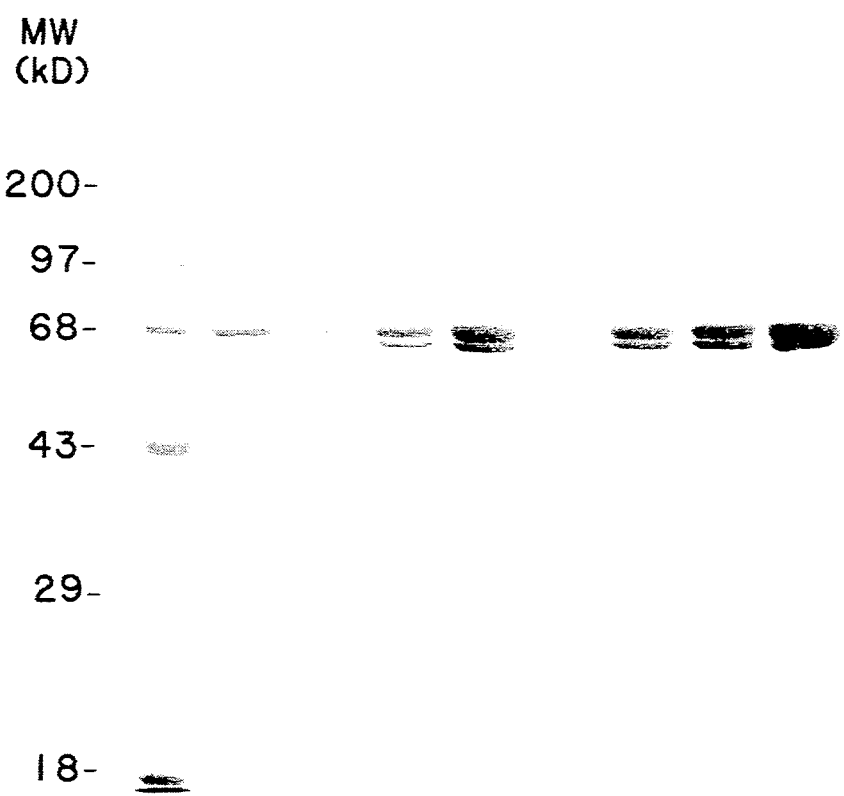
FIG. 12 shows the results of SDS-PAGE analysis of purified Coleopteran toxin from Btt.
Figure 13:
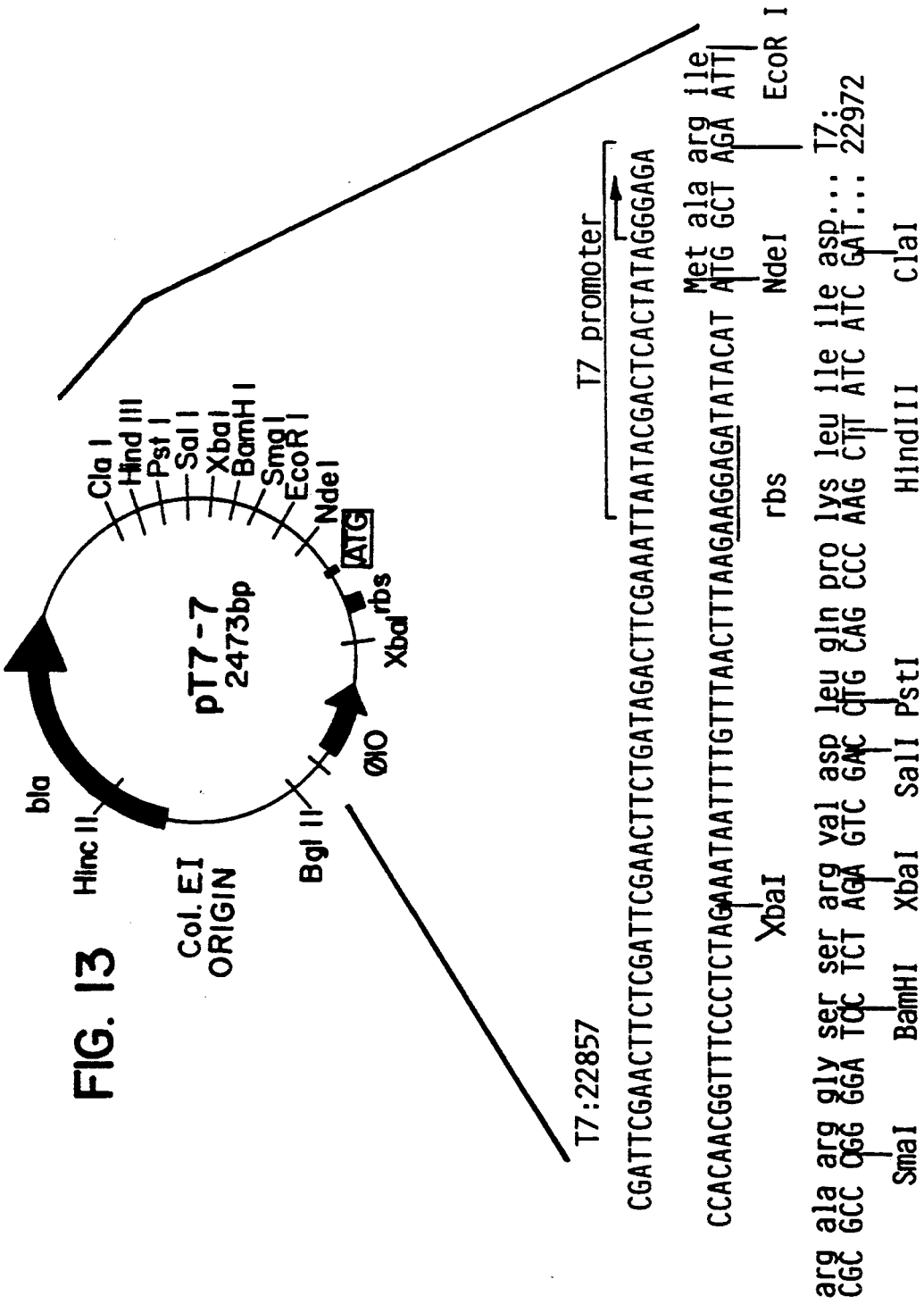
FIG. 13 is a restriction endonuclease map of plasmid pT7-7.
Figure 15:
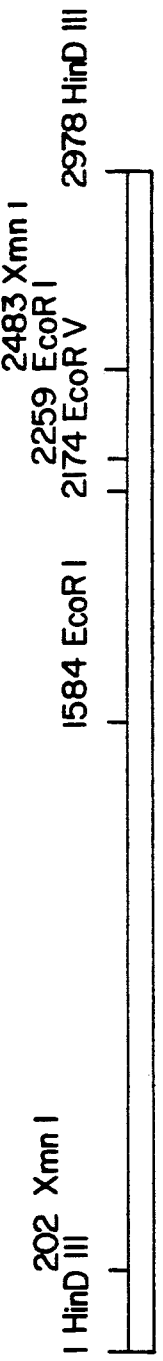
FIG. 15 shows the restriction maps of Btt toxin gene.
Figure 19:
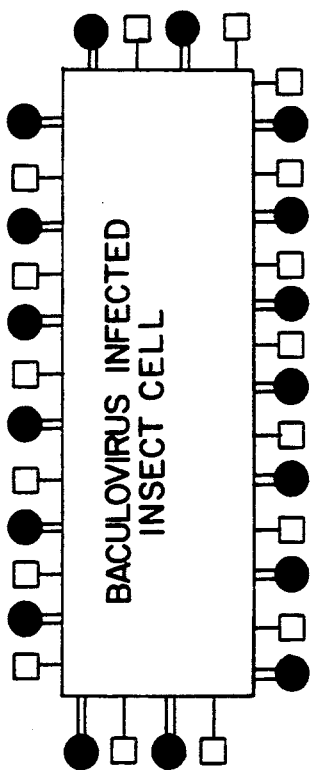
FIG. 19 illustrates a Baculovirus infected insect cell with gp64 surface protein and adjacent insecticidal toxin protein molecules on its surface.

Membrane vesicles from brush border epithelial cells were isolated by the following way as described by Wolfersberger, M. et al., supra. The isolated midguts from *Trichoplusia ni* larvae were mixed with buffer A (1:9 wt/vol) and blended with a Sorvall Omni-mixer twice, each time for 90 sec with medium speed, with one minute intervals. After blending, an equal volume of cold 24 mM MgC12 was added, mixed well with the blender for 90 sec. additionally and let it stand on ice for 15 min. Then the solution was spun at 2500X g for 15 min in a Sorvall centrifuge with the SS-34 rotor at 4° C. The supernatant was removed and spun in a separate tube at 30,000X g for 30 min in the same rotor. The above high speed pellet was resuspended in 0.5 original homogenate volume of buffer A with a teflon hand homogenizer, equal volume of cold 24 mM MgC12 was added, mixed well with a blender for 90 sec and let it stand on ice for 15 min as before. Then the homogenate was spun at 2500 × g for 15 min and at 30,000 × g for 30 as described above. The thus obtained membrane vesicle pellet was resuspended in 0.5 × concentration buffer A at about 3-5 mg/ml and stored at −80° C. as 15μl aliquots. The enrichment of brush border membrane vesicles in the final pellet was inferred by the 10 times higher specific activity of alkaline phosphatase in the final pellet than the initial 2500 × g pellet. In our hands the membrane vesicles were active in binding experiments for at least 4-6 months and new batch of vesicles were made after that.

b. I-125 radiolabeling of the surface proteins of the AcMNPV:

Viral surface proteins were labeled with Iodine-125 by using Iodo-Gen according manufacturer's instructions (Pierce). Iodo-Gen was dissolved in chloroform at 0.1 mg/ml and about 10μg of Iodo-Gen was coated to about 1.5 cm height of the 11mm disposable glass tube by gently rotating the tube on its side in presence of a thin jet of nitrogen to evaporate chloroform. Unused Iodo-Gen coated tubes were stored at 4° C. in desiccator till use (usually 3-4 weeks). Iodination was performed in fume-hoods by incubating about 50-75μg viral protein (100μl volume in PSB+Ca+MG buffer) in Iodo-Gen coated tubes in presence of 0.3-0.5 mCi of carrier-free Iodine-125 at room temperature for 30-40 min with occasional shaking of the tubes. Labelling was stopped by transferring the sample to 8ml Beckman polyallomer clear tubes kept at 4° C. Free Iodine-125 was removed from the viral proteins by filling up the centrifuge tubes with 6.5ml of cold PBS+Ca+Mg buffer and centrifuging the samples at 25K rpm in a 60 Ti rotor at 4° C. for 60 min. Viral pellet was washed twice with 7 ml of same cold buffer and spun for 60 min each time at 25K rpm as described above. Iodine-125 free viral pellet was resuspended in a small volume of PBS+Ca+Mg buffer (100-300μl), homogenized with a 0.5 ml ounce glass homogenizer (10-15 strokes), spun the sample in a microfuge at 13,000 rpm for 10 min at 4° C., the supernatant was carefully removed and stored as 100μl aliquots at −20° C. till use.

c. Binding assay:

Brush Border Membrane Vesicles (5-10 μg/assay) were incubated in a final volume of 400 μl PBS+Ca+Mg buffer with 100-200K cpm iodine-125 labeled viral protein. Membrane vesicles were not added to control tubes. The tubes were incubated in a waterbath maintained at 20° C. for 60 min before the binding was terminated by spinning the samples in a microfuge at 4° C. at 13K rpm for 5 min. The supernatants were carefully removed and the membrane vesicle pellets were washed twice each time with a brief vortexing and resuspension in 0.5 ml of PBS+Ca+Mg buffer containing 0.1 mg/ml BSA (buffer B) and centrifuged as above. The washed pellet was resuspended in a 150 μl volume of buffer B, 3 ml of Nugene liquid scintillant was added, mixed well and counted in a Beckman LSS liquid scintillation counter with the energy window completely open. Viral binding was expressed as cpm bound to membrane vesicles/assay.

d. Generation of polyclonal antibodies against Btt:

One of the major tools required for this study is antibodies to Btt protein. In order to detect the Btt and Btt/gp64 fusion protein in *E. coli* polyclonal antibodies are necessary and was generated by the following method. Initially, the Btt protein was purified from Btt itself and the purified protein was first analyzed on SDS-PAGE (FIG. 12). This purified protein was later injected several times into two rabbits and thus the polyclonal antibodies were made. These antibodies were checked and confirmed for its titre, immunospecificity against Btt and BTT/gp64 fusion. Direct Enzyme-Linked Immunosorbent Assay (ELISA) (Engvall, E. and Perlman, P., *Immunochem.* 8, 871-879 (1971)) is used for detection of Btt antibodies in test serum. Briefly, the antigen Btt or Btt-gp64 fusion proteins were first adsorbed on the well surfaces of microtiter plates. Serum samples from rabbit test bleeds were diluted at different concentrations and incubated in separate antigen coated wells. Antigenspecific antibody present in the serum samples will bind to the antigen. Unbound serum or supernatant components were washed away, and alkaline phosphatase conjugated anti-rabbit IgG was then bound to rabbit antibodies already bound to antigen. Excess conjugate was washed away, and substrate paranitrophenol solution is added to each well. The amount of color developed as the substrate acted upon by the enzyme of the conjugate is directly proportional to the amount of antibody in the serum.

B. CLONING AND EXPRESSION OF DELTA ENDOTOXIN GENES FROM BTT

One of the tools required for this gene fusion study is to obtain the genes coding for delta endotoxins from strains which are toxic to lepidopterans and coleopteran beetles. We have chosen Coleopteran BT toxin *Bacillus thuringiensis tenebrionis,* Btt) over Lepidopteran BT toxin for several reasons. One among them is, since the gp64 is from a virus which infects exclusively lepidopteran hosts, when fused with the coleopteran toxin, it will be easier to assay the chimeric toxin protein for its newly acquired toxicity against lepidopteran larvae (*Trichoplusia ni*). For obtaining the gene coding for the coleopteran toxin, Bacillus thuringiensis tenebrionis (Btt) was obtained from Safer Inc., Newton, Mass. utilizing the published sequence of Btt protein [Hofte, H. et al., *Nucleic Acid Research*, 15, 7183 (1987)]. Two oligonucleotides (26mer and a 31mer) of the following sequences: 26mer 5'-A A G C T T A C A G A A A T A C A C G A G G G C - 3'; 31 m e r -5'AAGCT-TAATTAAAGATAATATCTTTGAATTG-3' were designed and made in order to synthesize the 2.98 kbp coleopteran toxin gene using the polymerase chain reaction (PCR) technique. Although the PCR experiments were initially successful, later experiments failed due to the unstable nature of Taq DNA polymerase. Hence, a recombinant pUC13 library was established using the HindIII fragments of total Btt DNA. The two oligonucleotides (26mer and 31mer) which were once designed for PCR were used as probes to screen the colonies chromosomal and plasmid) was isolated from the bacterial strain *Bacillus thuringiensis tenebrionis* (Btt). (This strain was obtained from Safer Inc. Isolated bacterial DNA was then digested with the restriction enzyme HindIII and the resulting small DNA fragments were mixed with the HindIII digested, dephosphorylated pUC13 plasmid DNA vector and T4 DNA ligase was added to facilitate the DNA ligation between the pUC13 vector and 'foreign' DNA fragments. The ligated DNA was then transformed into an *E. coli* strain MM294 and the bacterial cells were plated on LB-Agar plates. Approximately, 700 transformed *E. coli* colonies were streaked on circular nitrocellulose paper and were allowed to grow on nutrient agar plates by placing the paper on top of the nutrient agar. After they were grown overnight, the nitrocellulose paper containing *E. coli* colonies were processed to lyse and fix the liberated DNA onto the paper. The nitrocellulose paper was then subjected to DNA hybridization using the radiolabeled (32P) Btt toxin specific oligonucleotides (26mer & 31mer) as the probes. Three colonies that hybridized to the probe (pUC7-1, pUC9-10 and pUC12-7) were identified to contain a pUC13 plasmid with the expected 2.98 kbp HindIII DNA fragment at the HindIII site of pUC13. After establishing the restriction map of this fragment with few restriction enzymes, it was confirmed that the pUC12-7 and pUC9-10 had the Btt gene in the right orientation and pUC7-1 had the gene in the opposite orientation. Later, toxicity experiments (with colorado potato beetles) were carried out with these clones (pUC12-7 & pUC7-1) and the results further confirmed the identity of the Btt clones (Table 1).

TABLE I

The activity of protein extracts on 6 day old Colorado potato beetle larvae during a 4 day exposure.

| Treatment | Mean % Mortality (S.D.) | % Area of Leaf Consumed (S.D.) |
|---|---|---|
| pUC13 | 3.3a (10.6) | 21.0a (8.1) |
| 12-7 uninduced | 36.7b (24.7) | 2.7c (1.8) |
| 12-7 induced | 33.3b (35.0) | 2.4c (1.8) |
| 7-1 induced | 30.0b (24.7) | 5.1c (4.8) |
| $H_2O$ control | 0a | 27.0b (8.9) |

Means followed by similar letters do not vary significantly ($\alpha$ = 0.05; SNK).

TABLE II

The activity of protein extracts (diluted to 50% with distilled water) on 6 day old Colorado potato beetle larvae during a 4 day exposure.

| Treatment | Mean % Mortality (S.D.) | % Area of Leaf Consumed (S.D.) |
|---|---|---|
| 50% 12-7 uninduced | 46.7 | 2.8a (1.9) |
| 50% 12-7 induced | 40.0 | 3.5a (5.0) |
| 50% 7-1 induced | 13.3 | 11.8a (19.0) |
| $H_2O$ control | — | 36.8b (31.4) |

Means followed by similar letters do not vary signficantly ($\alpha$ = 0.05; SNK).

High Level Expression of Btt Gene in *E. coli*

Although pUC 12-7 was toxic to coleopteran larvae (Table 1), we could not detect the 66kD 0r 72KD Btt toxin protein on a comassie-Blue stained SDS-PAGE. This indicated to us that the Btt toxin is made in very small amounts since the expression is driven by Btt promoter. Since future experiments also (Btt/gp64 fusions) require high level expression, we decided to express the Btt protein in large amounts in *E. coli* using an expression plasmid pT7-7 which has a strong T7 bacteriophage promoter (FIGS. 7 and 13). Initially, the Btt toxin gene from pUC12-7 was first subcloned into pT7-7 vector (a T7 promoter based vector for expressing foreign genes) and the coleopteran toxin was expressed in vivo in *E. coli* both as a fusion protein with T7 phage gene 10 protein amino terminus (pT7-SX12 and pT7-X9) and as a non-fusion native Btt toxin protein (pT7-4-4). All these recombinant plasmids were transformed into a *E. coli* strain BL21 [Studier, F. W., & B. A. Moffatt, *J. Mol. Biol.*, 189, 113–130 (1986)]which carries a structural gene coding for T7 RNA polymerase protein. This gene is under the control of lacZ promoter and the recombinant Btt can be expressed by inducing with IPTG. These recombinant plasmids expressed the Btt toxin to higher levels than pUC12-7 and were also toxic to coleopteran larvae (FIG. 8 & Table 2).

TABLE 2

Efficacy of protein extracts on 10 day old CPB larvae, *Leptinotarsa decemlineata*. Larvae kept on treated leaves for 4 days.

| Treatment | Mean % Area Consumed (SD) | % Mortality |
|---|---|---|
| $H_2O$ | 40.3 (27.6) b | 0 |
| #T7-7 (100%) | 36.9 (20.3) b | 0 |
| #X-9 (100%) | 1.9 (0.7) a | 50 |
| #X-9 (50%) | 3.0 (1.4) a | 50 |
| #X-9 (10%) | 6.6 (8.5) a | 0 |
| #4-4 (100%) | 2.0 (1.9) a | 40 |
| #4-4 (50%) | 2.0 (0.8) a | 30 |
| #4-4 (10%) | 6.5 (3.9) a | 10 |
| #12-7 (100%) | 1.1 (—) a | 90 |
| #12-7 (50%) | 2.6 (0.7) a | 40 |
| #12-7 (10%) | 4.0 (2.1) a | 0 |

Means followed by same letter are not significantly different ($\alpha$ = 0.05, SNK).

Conclusions

No significant difference was observed between the protein extracts in the mean percent area consumed, though it was significantly less from both control treatments. Mortality of the larvae was considerably higher for the #12-7 extract, which is indicative of an active toxin.

Construction and Expression of Btt/gp64 Gene Fusions

After constructing the above recombinant plasmids which expresses the Btt toxin proteins in *E. coli,* Btt/gp64 gene fusions were constructed. The strategy for these recombinant DNA fusions are shown in FIG. 9. A unique XmnI restriction site at the coding region of the carboxyl terminus of Btt protein was cleaved and the polylinker containing the multiple restriction sites was positioned near the XmnI site through DNA ligation. Utilizing the polylinker restriction sites, three different Btt/gp64 gene fusions (pFAv10, pFX7 & pFAc13) were constructed and are shown in FIG. 9. All these recombinant plasmids were transformed into a *E. coli* strain BL21 which carries a structural gene coding for T7 RNA polymerase protein. This gene is under the control of lacZ promoter and the recombinant Btt/gp64 gene fusions can be expressed by inducing with IPTG. Immunoblotting experiments with these Btt/gp64 fusion proteins indicate that all the fusion proteins were expressed but at a lower level when compared to Btt itself (FIG. 10).

E. Toxicity Bioassays a) Toxicity bioassays with Btt/gp64 fusion proteins were carried out against *Trichoplusia ni* neonate larvae. Basically these experiments were done with lima beans artificial diet. We grew large batches of *E. coli* cultures which expresses these fusion proteins and identical amounts of control *E. coli* pT7-7 and E. coli Btt/gp64 pFAv10 were mixed respectively with the identical amounts of lima beans diet to maintain the same concentration of protein. Neonate larvae of *Trichoplusia ni* were allowed to feed on these diets and after 6 days, the mortality due to toxicity was recorded. Control pT7-7 showed 34% mortality while the pFAv10 which expresses the 125kD Btt/gp64 fusion protein exhibited 55% mortality. The experiments were done only with one high dose. When observed, the surviving larvae on the Btt/gp64 fusion diet were comparatively small, sick and lethargic. The pictures of these surviving larvae and is shown in FIG. 11. Also, we looked at the midguts of several surviving larvae under a phase contrast light microscope and widespread damage of the midgut was observed in the Btt/gp64 fed larvae when compared to the control pT7-7 fed larvae, indicating that the chimeric Btt/gp64 toxin has interacted and disturbed the ionic flow across the membrane. Histopathological studies are in progress to determine the exact nature of the gut damage. In addition, earlier toxicity bioassay experiments with slightly lower concentrations of Btt/gp64 fusion proteins also exhibited this toxicity. These experiments clearly indicate that the Btt/gp64 fusion protein has acquired the new toxicity towards lepidopteran larvae and might have caused the gut damage.

b) Toxicity bioassays against *Heliothis virescens* larvae were done with purified inclusion bodies of Btt-gp64 fusion proteins. Respective *E. coli* cells containing Btt-gp64 expression plasmids pSX12T, pFAv10, pFx7 and pFAc13 were grown in large batches (5 liters) of media. Cells were pelleted, washed with 0.2M sodium phosphate buffer pH 6.0, and resuspended in 15 ml phosphate buffer and 1 mM PMSF. Cells were lysed at 11,000 psi in a French Pressure cell and the soluble proteins were removed by pelleting the insoluble protein at 15,000 X g for 30 minutes in an SS34 rotor. Pellets were resuspended in 30 ml phosphate buffer containing 1 mM PMSF, incubated for 5 minutes on ice, and spun again. The inclusion body pellet was resuspended in Renograffin solution (1.8 times diluted) and the Renograffin gradients were centrifuged at 30,000 × g for 1 hour in a SW28 rotor. After the spin, the Renograffin solution was poured through a cheesecloth to remove the top gelatinous layer, and the gradient supernatant was diluted with at least 2 volumes of cold 10mM EDTA (pH 8.0). Samples were spun at 15,000 × g for 30 minutes (SS34 rotor), followed by three washes in 10mM EDTA and one wash in distilled water. The final inclusion body pellet was resuspended in water for toxicity bioassays.

Protein concentrations of individual Btt-gp64 fusion protein inclusion body were determined by Bradford assay. Forty milligram samples of each protein (32.2 mg of pFAvl0) were resuspended in 1.0 ml water and 4.0g diet were added. Neonate *Heliothis virescens* larvae were placed on the diet and incubated for 5 days at 28° C. Individual animals were weighed and the average weights were determined.

| Sample Protein | Average Bodyweight |
| --- | --- |
| Water Control | 56.2 mg |
| pSX12T Control | 54.8 mg |
| pFAv10 fusion protein | 16.3 mg |
| pFX7 | 30.7 mg |
| pFAc13 | 38.3 mg |

Figure 23:
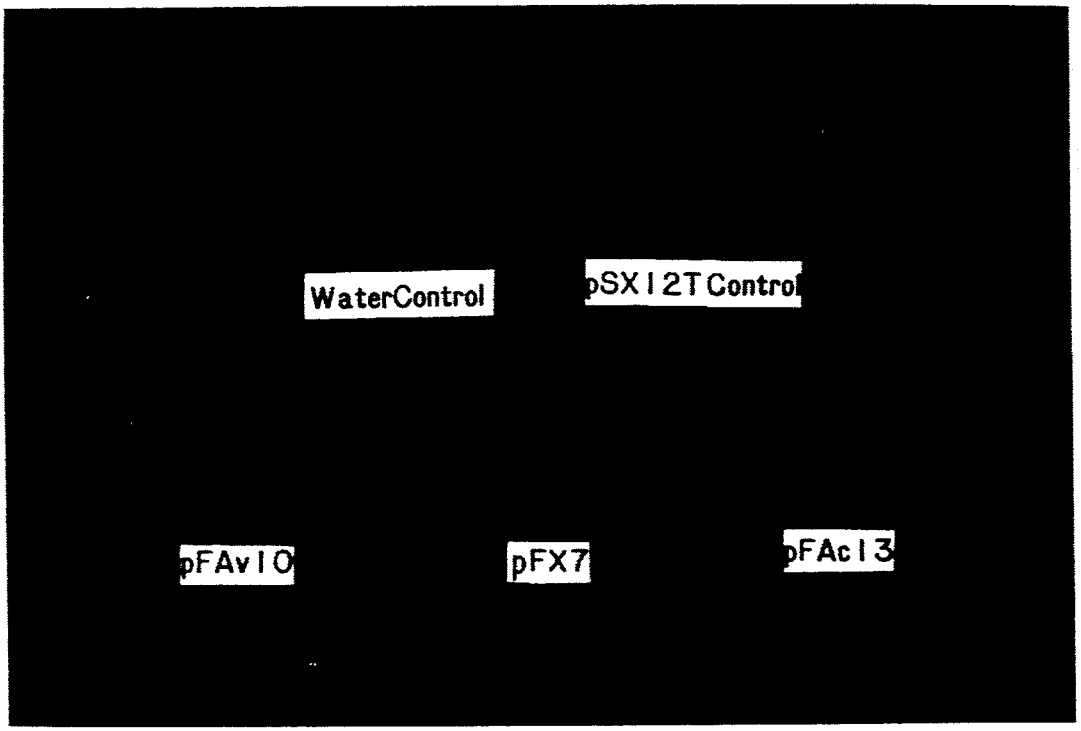
Figure 24:
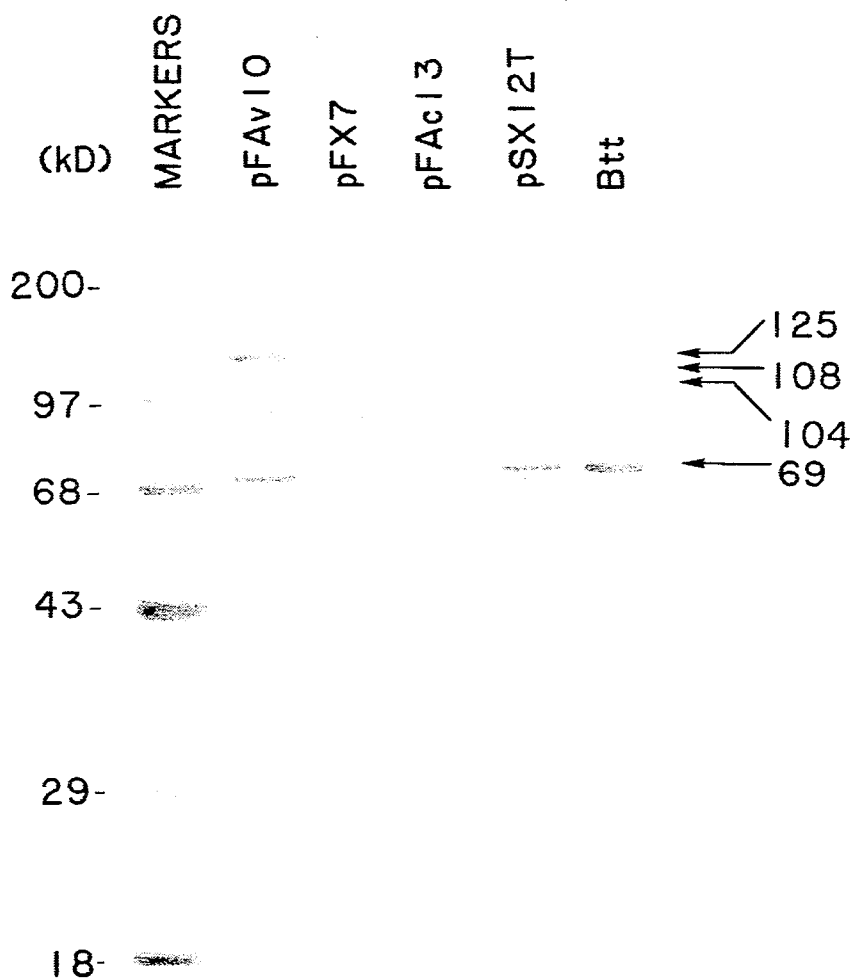

These results indicate that the Btt-gp64 fusion protein are toxic to lepidopteran Heliothis larvae and among them pFAv10 is most toxic (see FIG. 23). It should be noted that in all the fusion protein inclusion body preparations (pFAv10, pFx7 and pFAc13) only 15% of the total proteins are undegraded full length fusion protein molecules because of protein degradation. However, in the control pSX12T non-fusion Btt protein, approximately 80% of the total protein is undegraded full length Btt protein molecules (see FIG. 24). Thus the Btt-gp64 fusion proteins possess higher toxicity against lepidopteran larvae than the nonfusion coleopteran Btt toxin protein. Additional precise protein engineering had to be done in order to further increase the toxicity of Btt-gp64 fusion proteins against the lepidopteran larvae. Thus these experiments prove the concept that an insect midgut binding domain of a protein can increase the host range of insecticidal proteins.

Example 2

Construction of a chimeric BT Cry-Cyt A gene a. Cloning of the Cry IV D gene.

The plasmid pMI [Galjart et al., *Curr. Microbiol.* 16, 171-174 (1987)]was prepared in large amounts (maxipreps) and then purified on a CsCl gradient according to standard procedures (Maniatis et al., Supra. After dialysis, electrophoretic and spectrophotometric analyses were performed to ensure the absence of degradation and determine the concentration of plasmid DNA in the sample. Then 10 μg of DNA was digested first in 20 μl (5 samples) with 50 units of EcoRV (Boehringer Mannheim) for 3 hr at 37° using the buffer recommended by the supplier. After adjustment of the sample volume to 30 μl with buffer, the samples were digested with 50 μl of Cla I at 37° C. for 3 hr using the buffer recommended by the supplier (Boehringer Mannheim). Proteins were eliminated by treatment with a mixture of phenol-chloroform-isoamyl alcohol and the sample DNA was precipitated with cold ethanol at −80° C. for 30 min (Maniatis et al. Supra) after which the DNA was resuspended in sterile double distilled water at a concentration of 100 ng/μl. Then 10 μl of the plasmid pBR322 was digested with EcoRV and ClaI in a similar manner. After phenolchloroform-isoamyl alcohol extraction and precipitation, the DNA was resuspended in 20μl of sterile double distilled water. Dephosphorylation of the DNA fragment ends was performed in a final volume of 50 μl using 3 units of calf intestine alkaline phosphatase by incubation at 37 ° C for 15 min and at 50° C. for 30 min in the buffer recommended by the supplier (Boehringer Mannheim). After addition of 3 more units of enzyme, the incubation cycle was repeated. The enzyme was removed by 3 phenol-chloroform isoamyl extractions, the DNA was precipitated with cold ethanol and resuspended in sterile double distilled water at a concentration of 100 mgμl. The ligation was performed at 12 ° C. for 15 hr using T4 DNA ligase (Boerhinger Mannheim). the molar ratio between the insert (pM1 digested by EcoRV and ClaI) and the veotor (pBR322 digested by EcoRV and ClaI) was 5. Ligation was monitored by agarose gel electrophoresis. Competent bacteria cells (*Escherichia coli* strain JM 105) were prepared and transformed with the ligated plasmid using standard procedures. The bacteria were then grown one hour and plated on LB-agar medium (Maniatis et al., Supra) containing ampicillin (50 μg/ml). The bacteria were grown 15 hr at 37° C. and the recombinant clones individually picked and plated at the same position on a plate containing LB agar and ampicillin, and on another one containing LB agar and tetracycline (15μg/ml). Since the cloning sites are located within the tetracycline resistance gene, the clone carrying an insert are tetracycline sensitive. The tetracycline sensitive-ampicillin resistant clones were grown individually. Small amounts of plasmid DNA ("minipreps") were obtained using standard procedures. The DNAs were screened by digestion with EcoRI and double digestion with EcoRV and ClaI to select the recombinant pBR322 plasmid carrying the fragment containing the gene CryIVD. The selected clone, named pBGG35, was purified in large amounts by the maxiprep procedure and stored at −20° C.

b. Cloning of the Cyt A gene.

The plasmid pMI was digested with EcoRI using procedures and conditions similar to those described above employing the buffer recommended for this enzyme. After the proteins were removed with phenol-chloroform-isoamyl alcohol, the DNA was precipitated with cold ethanol and resuspended in sterile double distilled water at a concentration of 100 ng/μl. The *E. coli* plasmid vector pBLUESCRIPT KS (Stratagene) was digested with EcoRI and the ends were dephosphorylated as described above. After extraction of the proteins and precipitation of the DNA, the DNA was resuspended in sterile double distilled water at a concentration of 100 ng/μl. The ligation and transformation of bacteria were done following the procedure described above except that the bacterial strain used in this case was *E. coli* strain XL 1 Blue. The selection of the recombinant clones was done by adding X GAL (40 μg/ml) and IPTG (1 μM). Since the polylinker is located within the Lac Z gene, bacteria with the recombinant plasmid lose their ability to degrade X GAL in the presence of IPTG, and thus will yield white colonies instead of blue ones obtained with the native plasmid. After isolation of each recombinant clone, minipreps of DNA were prepared and the clones were screened by digestion with BamHI, EcoRV and PstI (Boehringer Mannheim) using conditions similar to those described above, each time using the recommended buffer. Two recombinant clones carrying the EcoRI insert containing the gene Cyt A in two different orientations were named pBBLe14e and pBBLe15e, and the DNA of these was prepared in large amounts by the maxiprep procedure. Then 2μg of the clone pBBLe15e was digested with 10 units of EcoRV to remove a non-essential fragment of the EcoRI insert, and then ligation was performed as described above without any previous dephosphorylation step. Subsequently, XL 1 Blue *E. coli* bacteria were transformed with the ligated plasmid using the same procedure and plated on LB agar containing ampicillin (50 μg/ml). A clone lacking the EcoRV fragment; was identified by digestion with EcoRV and BamHI (as described above) and named pBBLe15eRV. This recombinant plasmid was purified by the maxiprep procedure.

c. Cloning of the truncated Cry IV D gene in pBLUESCRIPT KS.

A quantity of 10 μg of the plasmid pBG35 was digested with 50 units of HaeIII (Boehringer Mannheim) at 37° C. for 3 hr in 20 μl (5X) using the buffer supplied with the enzyme. After monitoring the digestion by agarose gel electrophoresis, the proteins were extracted with a mixture of phenol-chloroform-isoamyl alcohol and the DNA was precipitated with cold ethanol. The DNA was then resuspended in sterile double distilled water at a concentration of 100 ng/μl. This digestion of pBG35 by HaeIII generated numerous fragments, one of about 3.5 kbp carrying the Cry IV D gene truncated 32 bp upstream from the stop codon as well as the promoter of this gene. Ten μg of pBLUESCRIPT KS was digested in a 20 μl (5X) with 50 units of SmaI at 25° C. for 3 hr and then treated with phenol-chloroform-isoamyl alcohol and the DNA precipitated with cold ethanol. The dephosphorylation was performed as previously described and the DNA was finally resuspended in sterile double distilled water at a final concentration of 100 ng/μl. Using procedures described above, the DNA insert (pBG 35 digested with HaeIII) was ligated in the vector (pBLUESCRIPT KS digested with SmaI) using a molar ratio between the insert and the vector of 5. The recombinant plasmid was transformed into competent XL 1 Blue *E. coli* bacteria. The bacteria were plated on LB agar containing ampicillin, IPTG and X GAL. The white colonies where collected individually and minipreps were prepared. The recombinant clones were screened by digestion with StyI (This enzyme does not cut pBLUESCRIPT KS, but there is a cleavage site for it n the Cry IV D gene ORF) and EcoRI to monitor the orientation. A clone, named pBBLh13s, was selected on this basis and the DNA was prepared by the maxiprep procedure.

d. Sequencing of the fusion between the 3'end of Cry IV D and the 5'end of the SmaI digested pBLUESCRIPT KS.

To ensure that the fusion between the Cry IV D gene and pBLUESCRIPT KS was in frame, the DNA was sequenced using the chain termination method. The sequencing system used was the SEQUENASE version 2.0 United States Biochemical Corporation). The sequencing was performed with double stranded DNA using the procedure described in the booklet delivered with the enzyme. The sequencing M13 reverse primer (5'-AACAGCTATGACCATG-3') was used to initiate the synthesis of the complementary strand which was labeled with dATP-$^{35}$S (Amersham). The fragments were separated with a BRL model S2 sequencing apparatus. The dried gel was placed on a Kodak X-OMAT film and the sequence was read after an over-night exposure The sequence read on the complementary strand was the o following: 5'-//-CCTGCAGCCCC-CGATTCTTTT-//-3'This corresponds on the opposite strand of the sequence 5'-AAAAGAATCGGGGGCTGCAGG-//-3'where 5'-//GGGGG-//3' corresponds to the fusion between HaeIII site (5'-GG/CC-3') and SmaI site (5'-CCC/GGG-3').

e. Cloning of Cyt A into pBLUESCRIPT KS in frame with Cry IV D.

A quantity of 10 μg of pBBLe15eRV was digested with 50 units of HaeIII in 20 μl (5X) at 37° C. for 3 hr in the buffer recommended by the supplier (Boehringer Mannheim). The phenol extraction and DNA precipitation were done as already described and the DNA was resuspended in sterile double distilled water at a concentration of 100 ng/μl. Ten μg of PBBLh13s was digested in 20 μl (5X) with 50 units of EcoRV under conditions similar to those described above as well as for the phenol extraction, ethanol precipitation and dephosphorylation. The final concentration of the DNA resuspended in sterile double distilled water is also 100 ng/ml. The ligation was performed at 12° C. for 15 hr using 2 units of T4 DNA ligase and the recommended buffer. The molar ratio between the insert (pBBLe15eRV digested with HaeIII) and the vector (pBBLh13s digested with SmaI) was 5. The ligation was monitored by agarose gel electrophoresis, and competent XL 1 Blue *E. coli* bacteria were transformed as described above and plated on LB agar containing ampicillin. The recombinant clone carrying both Cry IV D and Cyt A in the correct orientation was screened using Sty I, Pst I and BamHI under the conditions specified by the supplier (Boehringer Mannheim).

Notwithstanding that reference has been made to particular embodiments, it will be understood that the present invention is not to be construed as limited to

We claim:

1. A method for increasing the host range or toxicity of an insecticidal protein or a protein domain exerting its activity via interaction with the gut epithelium of insects within its host range, comprising delivering said insecticidal protein or protein domain to the gut epithelium of a target insect with the aid of a targeting protein or protein domain capable of binding to said gut epithelium of said target insect.

2. The method of claim 1 wherein said targeting protein or protein domain being originated from a source other than Bacillus thuringiensis.

3. The method of claim 1 wherein said target insect is within the host range of said insecticidal protein.

4. The method of claim 1 wherein said target insect is outside the host range of said insecticidal protein.

5. The method of claim 1 wherein said insecticidal protein is an insecticidal crystal protein or a fragment thereof having insecticidal activity.

6. The method of claim 5 wherein said insecticidal protein is a crystal protein of Bacillus thuringiensis (B. thuringiensis), or a fragment thereof having insecticidal activity.

7. The method of claim 6 wherein said insecticidal protein is the crystal protein of a Coleopteran-specific B. thuringiensis.

8. The method of claim 7 wherein said insecticidal protein is the toxic domain of a B. thuringiensis subsp. tenebriosis crystal protein.

9. The method of claim 2 wherein said targeting protein is a viral surface protein or a fragment thereof having insect gut binding ability.

10. The method of claim 9 wherein said viral surface protein is a surface glycoprotein of the extracellular form of a nuclear polyhedrosis virus.

11. The method of claim 10 wherein said surface glycoprotein is the gp64 glycoprotein of the extracellular form of Autooraoha californica Nuclear Polyhedrosis Virus (AcNPV).

12. The method of claim 9 wherein said viral protein is a surface coat protein of a plant virus.

13. The method of claim 12 wherein said plant virus is a luteovirus.

14. A method for increasing the host range or toxicity of an insecticidal protein or a protein domain exerting its activity via interaction with the gut epithelium of insects within its host range, comprising delivering said insecticidal protein or a protein domain to the gut epithelium of a target insect with the aid of a targeting bacterial protein or protein domain having high affinity for the lipid components of membranes.

15. The method of claim 14 wherein said insecticidal protein is a crystal protein of Bacillus thuringiensis (B. thuringiensis) or a fragment thereof having insecticidal activity.

16. The method of claim 15 wherein said insecticidal protein comprises the toxic domain of a B. thuringiensis tenebriosis crystal protein.

17. The method of claim 15 wherein said bacterial protein is an about 27.3-kDA cytolytic protein of B. thuringiensis or a fragment thereof having high affinity for lipid components of membranes.

18. The method of claim 17 wherein said bacterial protein is the about 25-kDA Cyt A protein, the protease resistant domain of an about 27.3-kDA cytolytic protein of B. thuringiensis subsp. israelensis or morrisoni.

19. The method of claim 1 or claim 14 wherein said insecticidal protein is delivered to the gut epithelium of said target insect in the form of a chimeric protein comprising said insecticidal protein or protein domain and said targeting protein.

20. The method of claim 19 wherein said chimeric protein comprises a crystal protein of Bacillus hurinoiensis (B. thuringiensis) or a fragment thereof having insecticidal activity and a surface glycoprotein of the extracellular form of a nuclear polyhedrosis virus or a fragment thereof having insect gut binding ability.

21. The method of claim 20 wherein said chimeric protein comprises the toxic domain of a B. thuringiensis tenebriosis crystal protein and the gp64 glycoprotein of the extracellular form of Autographa californica Nuclear Polyhedrosis Virus (AcNPV).

22. The method of claim 19 wherein said chimeric protein comprises the toxic domain of a B. thuringiensis crystal protein and an about 27.3-kDA cytolytic protein of B. thuringiensis or a fragment thereof having high affinity for lipid components of membranes.

23. The method of claim 22 wherein said chimeric protein comprises the toxic doman of a B. thuringiensis crystal protein and the about 25-kDA Cyt A protein, the protease resistant domain of an about 27.3-kDA cytolytic protein of B. thuringiensis subsp. israelensis or morrisoni.

* * * * *

Adverse Decisions in Interference

Patent No. 5,143,905, Natarajan Sivasubramanian, Brian A. Federici, METHOD AND MEANS FOR EXTENDING THE HOST RANGE OF INSECTICIDAL PROTEINS, Interference No. 103,766, final judgment adverse to the patentees rendered December 11, 1997, as to claims 1-13, 19/1,20 and 21.
*(Official Gazette April 21, 1998)*

Disclaimer and Dedication

5,143,905 - Natarajan Sivasubramanian; Brian A. Federici, both of Riverside, Calif. METHOD AND MEANS FOR EXTENDING THE HOST RANGE OF INSECTICIDAL PROTEINS. Patent dated September 1, 1992. Disclaimer and dedication filed January 26, 1998, by the assignee, The Regents of the University of California.

Hereby disclaims and dedicates to the Public claims 1-13, 20 and 21 of said patent.
*(Official Gazette,* November 16, 1999)